US006642025B2

(12) United States Patent
Murdin et al.

(10) Patent No.: US 6,642,025 B2
(45) Date of Patent: Nov. 4, 2003

(54) CHLAMYDIA ANTIGENS AND CORRESPONDING DNA FRAGMENTS AND USES THEREOF

(75) Inventors: Andrew D. Murdin, Ontario (CA); Raymond P. Oomen, Ontario (CA); Pamela L. Dunn, Ontario (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/905,119

(22) Filed: Jul. 13, 2001

(65) Prior Publication Data

US 2002/0091096 A1 Jul. 11, 2002

Related U.S. Application Data

(62) Division of application No. 09/427,501, filed on Oct. 26, 1999, now Pat. No. 6,403,101.

(60) Provisional application No. 60/154,658, filed on Sep. 20, 1999, and provisional application No. 60/106,037, filed on Oct. 28, 1998.

(51) Int. Cl.[7] ................................................ C12P 21/06

(52) U.S. Cl. .................... 435/69.1; 536/23.1; 536/23.7; 536/24.1; 536/24.2; 536/24.32; 435/320.1; 435/69.3; 435/71.1; 435/71.2; 435/69.7; 435/69.8

(58) Field of Search ............................... 536/23.1, 23.7, 536/24.1, 24.2, 24.32; 435/320.1, 69.1, 69.3, 71.1, 71.2, 69.7, 69.8

(56) References Cited

U.S. PATENT DOCUMENTS 6,403,101 B1 * 6/2002 Murdin et al.

OTHER PUBLICATIONS

Kalman et al. Nature Genetics. 1999. 21: 385–389.*

Magee et al. Infection and Immunity. 1995. 63(2): 516–521.*

* cited by examiner

*Primary Examiner*—Jennifer E. Graser

(74) *Attorney, Agent, or Firm*—Ivor R. Elrifi; Nicholas P. Triano, III; Mintz, Levin, Cohn, Ferris, Glovsky and Popeo, P.C.

(57) ABSTRACT

In summary of this disclosure, the present invention provides a method of nucleic acid, including DNA, immunization of a host, including humans, against disease caused by infection by a strain of Chlamydia, specifically *C. pneumoniae*, employing a vector, containing a nucleotide sequence encoding a lorf2 protein of a strain of *Chlamydia pneumoniae* and a promoter to effect expression of the lorf2 gene in the host. Modifications are possible within the scope of this invention.

10 Claims, 11 Drawing Sheets

```
atgtttgttt cttgtagctc agtcgctttc ttttagcttt aagttttgat agcctgcttg 60

gtcttctgtt tctacactta atattgatac taaggatact atg aaa aaa cag gta   115
                                            Met Lys Lys Gln Val
                                             1               5

tat caa tgg tta gcg agt gtg gtt ctt tta gcg ctg aca att tca gga   163
Tyr Gln Trp Leu Ala Ser Val Val Leu Leu Ala Leu Thr Ile Ser Gly
                10                  15                  20

tac gct gaa ctt cct ctc tcg gaa caa aaa gta aaa agt cac act tat   211
Tyr Ala Glu Leu Pro Leu Ser Glu Gln Lys Val Lys Ser His Thr Tyr
            25                  30                  35

aca act tta gac gaa gtc aaa gac tac tta agt aaa cgg ggt ttt gta   259
Thr Thr Leu Asp Glu Val Lys Asp Tyr Leu Ser Lys Arg Gly Phe Val
        40                  45                  50

gaa acg cga aag caa gat ggc gtt tta aga ata gca gga gat gtt aga   307
Glu Thr Arg Lys Gln Asp Gly Val Leu Arg Ile Ala Gly Asp Val Arg
    55                  60                  65

gcc cgg tgg ttg tat ttc aga gaa gat atc aaa aac ccc tca gat aaa   355
Ala Arg Trp Leu Tyr Phe Arg Glu Asp Ile Lys Asn Pro Ser Asp Lys
70                  75                  80                  85

gat aaa tac aat ccc tta cca gta aat cgt tat cgt agt gaa ttt tat   403
Asp Lys Tyr Asn Pro Leu Pro Val Asn Arg Tyr Arg Ser Glu Phe Tyr
                90                  95                  100

ctc tat att gat tat cgc gct gag agg aac tgg ctg tct tca aag atg   451
Leu Tyr Ile Asp Tyr Arg Ala Glu Arg Asn Trp Leu Ser Ser Lys Met
            105                 110                 115

aat tgg aca gca att gca gga ggg gaa aac act gca gct ggt gtt gat   499
Asn Trp Thr Ala Ile Ala Gly Gly Glu Asn Thr Ala Ala Gly Val Asp
        120                 125                 130

atc aac aga gca ttt cta gga tat cgt ttt tat aag aat ccc gaa aca   547
Ile Asn Arg Ala Phe Leu Gly Tyr Arg Phe Tyr Lys Asn Pro Glu Thr
    135                 140                 145
```

FIG. 1A

```
cgt aca gat ttc ttt atg gaa atc gga cgt tct ggt tta gga gat ctc     595
Arg Thr Asp Phe Phe Met Glu Ile Gly Arg Ser Gly Leu Gly Asp Leu
150                 155                 160                 165

ttt gag tca gaa gtc caa ttc caa agt aat ttt gac gga cta cat ata     643
Phe Glu Ser Glu Val Gln Phe Gln Ser Asn Phe Asp Gly Leu His Ile
                170                 175                 180

tat tgg act cga gaa ctt tct aag gac tat cct tat caa gtg att gtt     691
Tyr Trp Thr Arg Glu Leu Ser Lys Asp Tyr Pro Tyr Gln Val Ile Val
            185                 190                 195

cat gga ggt cct ttc gtc gtg aac atg aca aaa aaa cat tat gct tgg     739
His Gly Gly Pro Phe Val Val Asn Met Thr Lys Lys His Tyr Ala Trp
        200                 205                 210

gtt gta gaa ggg att ctc aat cgt ttg cct aaa cag ttt ttt gtg aaa     787
Val Val Glu Gly Ile Leu Asn Arg Leu Pro Lys Gln Phe Phe Val Lys
    215                 220                 225

tgt agt gtt gtc gac tgg aac aca ttc gtt cct tca gaa acc tcc act     835
Cys Ser Val Val Asp Trp Asn Thr Phe Val Pro Ser Glu Thr Ser Thr
230                 235                 240                 245

aca gaa aaa gct gct aca aac gct atg aaa tac aaa tac tgt gtt tgg     883
Thr Glu Lys Ala Ala Thr Asn Ala Met Lys Tyr Lys Tyr Cys Val Trp
                250                 255                 260

cag tgg ctc gtc gga aag cat agt cag gtt cct tgg atc aat gga cag     931
Gln Trp Leu Val Gly Lys His Ser Gln Val Pro Trp Ile Asn Gly Gln
            265                 270                 275

aaa aag cct cta tat ctt tat gga gct ttc tta atg aac cct tta gca     979
Lys Lys Pro Leu Tyr Leu Tyr Gly Ala Phe Leu Met Asn Pro Leu Ala
        280                 285                 290

aag gct acg aag act acg tta aat gga aaa gaa aac cta gct tgg ttt    1027
Lys Ala Thr Lys Thr Thr Leu Asn Gly Lys Glu Asn Leu Ala Trp Phe
    295                 300                 305
```

FIG. 1B

```
att gga gga act tta ggg gga ctc aga aaa gct gga gac tgg tct gcc    1075
Ile Gly Gly Thr Leu Gly Gly Leu Arg Lys Ala Gly Asp Trp Ser Ala
310                 315                 320                 325

aca gta cgt tat gag tat gtc gaa gcc ttg tcg gtt cca gaa ata gat    1123
Thr Val Arg Tyr Glu Tyr Val Glu Ala Leu Ser Val Pro Glu Ile Asp
                330                 335                 340

gtt tca ggg att ggc cgt ggt aat tta tta aag ttt tgg ttc gcc caa    1171
Val Ser Gly Ile Gly Arg Gly Asn Leu Leu Lys Phe Trp Phe Ala Gln
            345                 350                 355

gca att gct gct aac tat gat cct aaa gag gct aat ggt ttt aca aat    1219
Ala Ile Ala Ala Asn Tyr Asp Pro Lys Glu Ala Asn Gly Phe Thr Asn
        360                 365                 370

tat aaa gga ttt tcc gct cta tat atg tat ggc atc aca gat tct cta    1267
Tyr Lys Gly Phe Ser Ala Leu Tyr Met Tyr Gly Ile Thr Asp Ser Leu
    375                 380                 385

tca ttc aga gct tat ggg gct tac tcc aaa cca gca aac gat aaa ctc    1315
Ser Phe Arg Ala Tyr Gly Ala Tyr Ser Lys Pro Ala Asn Asp Lys Leu
390                 395                 400                 405

ggc agt gat ttt act ttc cga aag ttt gat cta ggt ata att tca gcg    1363
Gly Ser Asp Phe Thr Phe Arg Lys Phe Asp Leu Gly Ile Ile Ser Ala
                410                 415                 420

ttt taagtcaaat tttaataaaa tctttaaaaa caggctcgca ttaattatta         1416
Phe

gtgagagctt ttttttattt ttttataata aaactaaaag atttttatta tttttgagt  1476

ttttatggtt aatcctattg gtccaggtcc tatagacgaa acagaacgca cacctcccgc  1536

agatctttct gctc                                                    1550
```

FIG. 1C

```
                                      Tth111II
                                  MseI    |       BbsI
               DdeI           AluI  |     |       Cac8I
              AluI|           CviJI |     |       MboII
             CviJI|     BseMII   |  |     |    CviJI |
                 ||         |    |  |     |        | |
    ATGTTTGTTTCTTGTAGCTCAGTCGCTTTCTTTTAGCTTTAAGTTTTGATAGCCTGCTTG
  1 ---------+---------+---------+---------+---------+---------+ 60
    TACAAACAAAGAACATCGAGTCAGCGAAAGAAAATCGAAATTCAAAACTATCGGACGAAC

                     SspI    DdeI
               MseI    | BciVI |
                  |    |     | |
    GTCTTCTGTTTCTACACTTAATATTGATACTAAGGATACTATGAAAAAACAGGTATATCA
 61 ---------+---------+---------+---------+---------+---------+ 120
    CAGAAGACAAAGATGTGAATTATAACTATGATTCCTATGATACTTTTTTGTCCATATAGT

                                Hpy178III
                               BciVI    |
                             Tsp509I |  |
                            HaeII  | |  |
                            HhaI|  | |  |
             DrdII   Eco47III|| |  | |  |              PpiI
                 |          ||| |  | |  |                 |
    ATGGTTAGCGAGTGTGGTTCTTTTAGCGCTGACAATTTCAGGATACGCTGAACTTCCTCT
121 ---------+---------+---------+---------+---------+---------+ 180
    TACCAATCGCTCACACCAAGAAAATCGCGACTGTTAAAGTCCTATGCGACTTGAAGGAGA

                                                           MseI
                                                       Sth132I
         MnlI       MaeIII                              AflII|
 Hpy188IX   |       Tsp45I                  Tth111I      SmlI|
        |   |            |                        |         ||
    CTCGGAACAAAAAGTAAAAAGTCACACTTATACAACTTTAGACGAAGTCAAAGACTACTT
181 ---------+---------+---------+---------+---------+---------+ 240
    GAGCCTTGTTTTTCATTTTTCAGTGTGAATATGTTGAAATCTGCTTCAGTTTCTGATGAA

        BscGI            ThaI        BccI   MseI
            |               |           |      |
    AAGTAAACGGGGTTTTGTAGAAACGCGAAAGCAAGATGGCGTTTTAAGAATAGCAGGAGA
241 ---------+---------+---------+---------+---------+---------+ 300
    TTCATTTGCCCCAAAACATCTTTGCGCTTTCGTTCTACCGCAAAATTCTTATCGTCCTCT
```

FIG. 2A

```
              Sth132I
          BanII     |
       Bsp1286I     |
           MspI     |
           NciI     |
          ScrFI     |              EcoRV     Hpy188IX      BseMII
      CviJI   |     | Hpy188IX Hin4I  | MboII DdeI  |   MnlI    |
            | |     |        |     |  |      |    | |      |    |
     TGTTAGAGCCCGGTGGTTGTATTTCAGAGAAGATATCAAAAACCCCTCAGATAAAGATAA
301  ---------+---------+---------+---------+---------+---------+ 360
     ACAATCTCGGGCCACCAACATAAAGTCTCTTCTATAGTTTTTGGGGAGTCTATTTCTATT

                                    ApoI                     MnlI
                                 Tsp509I               CjePI    |
               BsrI        Pfl1108I    |            BseMII  |ThaI
                  |               |    |                  | |   |
     ATACAATCCCTTACCAGTAAATCGTTATCGTAGTGAATTTTATCTCTATATTGATTATCG
361  ---------+---------+---------+---------+---------+---------+ 420
     TATGTTAGGGAATGGTCATTTAGCAATAGCATCACTTAAAATAGAGATATAACTAATAGC

                  BsrI                         CviRI
                CviJI|                       MnlI  |
    DdeI     BbsI   ||       Tsp509I       MunI |  |
   HhaI|    MboII   ||       CjePI |    Tsp509I |  | CjeI
      ||        |   ||           | |          | |  |    |
     CGCTGAGAGGAACTGGCTGTCTTCAAAGATGAATTGGACAGCAATTGCAGGAGGGGAAAA
421  ---------+---------+---------+---------+---------+---------+ 480
     GCGACTCTCCTTGACCGACAGAAGTTTCTACTTAACCTGTCGTTAACGTCCTCCCCTTTT

         AluI
        CviJI
      MspA1I
        PvuII
        PstI|
       TspRI|
     Fnu4HI||
     CviRI|||
      TseI|||      EcoRV                                Hpy178III
    BtsI ||||     BbvI |                               HinfI    |
    SfcI ||||  BsbI  | |   CjeI     BfaI EcoRV          TfiI    |
       | ||||     |  | |      |        |     |             |    |
     CACTGCAGCTGGTGTTGATATCAACAGAGCATTTCTAGGATATCGTTTTTATAAGAATCC
481  ---------+---------+---------+---------+---------+---------+ 540
     GTGACGTCGACCACAACTATAGTTGTCTCGTAAAGATCCTATAGCAAAAATATTCTTAGG
```

FIG. 2B

```
              RsaI
           BsaAI |                                            DpnI
          MaeII| |                                       BglII |
       Sth132I|| |                         MaeII         BstYI |
       AflIII|| | |                 Hpy188IX   |         Sau3AI |      HinfI
            |||| |                        |   |              | |         |
        CGAAACACGTACAGATTTCTTTATGGAAATCGGACGTTCTGGTTTAGGAGATCTCTTTGA
    541 ---------+---------+---------+---------+---------+---------+ 600
        GCTTTGTGCATGTCTAAAGAAATACCTTTAGCCTGCAAGACCAAATCCTCTAGAGAAACT

                                                       Hpy178III
                                                          TaqI |
                                                          AvaI| |
          Tsp509I                                         SmlI| |
        PleI     |                                        XhoI| |
    Hpy188IX |   |      Tsp509I               PleI HinfI   || |
           |  |   |          |                   |     |   || |
        GTCAGAAGTCCAATTCCAAAGTAATTTTGACGGACTACATATATATTGGACTCGAGAACT
    601 ---------+---------+---------+---------+---------+---------+ 660
        CAGTCTTCAGGTTAAGGTTTCATTAAAACTGCCTGATGTATATATAACCTGAGCTCTTGA

                                   AvaII
                                Eco0109I
                                   Psp5II
                                   Sau96I
                                Sse8647I
                              NlaIII |     Hpy178III
      DdeI        CjePI      MnlI    | |      CjePI|  NlaIII
         |             |        |    | |          ||        |
        TTCTAAGGACTATCCTTATCAAGTGATTGTTCATGGAGGTCCTTTCGTCGTGAACATGAC
    661 ---------+---------+---------+---------+---------+---------+ 720
        AAGATTCCTGATAGGAATAGTTCACTAACAAGTACCTCCAGGAAAGCAGCACTTGTACTG

                                HaeIV
                                Hin4I
                            HinfI   |
                             TfiI   |
    Tth111II                XmnI|   |                TaaI
           |                    ||   |                   |
        AAAAAAACATTATGCTTGGGTTGTAGAAGGGATTCTCAATCGTTTGCCTAAACAGTTTTT
    721 ---------+---------+---------+---------+---------+---------+ 780
        TTTTTTTGTAATACGAACCCAACATCTTCCCTAAGAGTTAGCAAACGGATTTGTCAAAAA
```

FIG. 2C

```
                         XmnI
                      BsrI   |
                  Eco57I |   |
             HincII     |  |   |
              AccI|     |  |   |
              TaqI|     |  |   |
             SalI||     |  |   |
          BsbI   |||     |  |   |       Hpy188IX        SfcI
             |   |||     |  |   |              |     BbvI |MnlI
    TGTGAAATGTAGTGTTGTCGACTGGAACACATTCGTTCCTTCAGAAACCTCCACTACAGA
781 ---------+---------+---------+---------+---------+---------+ 840
    ACACTTTACATCACAACAGCTGACCTTGTGTAAGCAAGGAAGTCTTTGGAGGTGATGTCT

                                                              CjeI
    Fnu4HI                                            Hpy188IX |
     AluI|                                          TspRI     |  |
    CviJI|                Tth111II      TaaI      CviJI|     |  |
     TseI|      MwoI      CjeI    |     MmeI|     BtsI  ||     |  |
        ||         |         |    |        ||        |  ||     |  |
    AAAAGCTGCTACAAACGCTATGAAATACAAATACTGTGTTTGGCAGTGGCTCGTCGGAAA
841 ---------+---------+---------+---------+---------+---------+ 900
    TTTTCGACGATGTTTGCGATACTTTATGTTTATGACACAAACCGTCACCGAGCAGCCTTT

                    DpnI
                Sau3AI |
             BsaJI   | |
              StyI   | |                                AluI
          NlaIV |    | |     AlwI      CviJI       MnlI    CviJI
              | |    | |        |          |          |        |
    GCATAGTCAGGTTCCTTGGATCAATGGACAGAAAAAGCCTCTATATCTTTATGGAGCTTT
901 ---------+---------+---------+---------+---------+---------+ 960
    CGTATCAGTCCAAGGAACCTAGTTACCTGTCTTTTTCGGAGATATAGAAATACCTCGAAA

                                                            AluI
                                         MboII              CjeI
                        Pfl1108I      MseI |               CviJI
                            CjeI|     BbsI  |  |              HgiEII
  MseI                    CviJI ||    MaeII  |  |CjeI        BfaI  |
     |                        | ||       |  |  |   |           |  |
    CTTAATGAACCCTTTAGCAAAGGCTACGAAGACTACGTTAAATGGAAAAGAAAACCTAGC
961 ---------+---------+---------+---------+---------+---------+ 1020
    GAATTACTTGGGAAATCGTTTCCGATGCTTCTGATGCAATTTACCTTTTCTTTTGGATCG
```

FIG. 2D

```
                                                    CjeI
                                                BseMII |
                                             BsmFI   | |
                       Hpy188IX        AluI|   | |                  BpmI
                 PleI     DdeI |   CviJI|   | |                     RsaI
    MnlI      CjeI |  HinfI  | |BsmAI ||   | | BsrI      TaaI |
       |         |  |       | | |     | ||   | |  |         | |
     TTGGTTTATTGGAGGAACTTTAGGGGGACTCAGAAAAGCTGGAGACTGGTCTGCCACAGT
1021 ---------+---------+---------+---------+---------+---------+ 1080
     AACCAAATAACCTCCTTGAAATCCCCCTGAGTCTTTTCGACCTCTGACCAGACGGTGTCA

                                                            BsaJI
                                                           BstDSI
                                                          CviJI|
                      CviJI                              HaeIII|
                       CjeI|   Hpy178III      BcefI        EaeI ||
 MaeII          TaqI   ||     NlaIV   |      CjePI        GdiII ||
     |             |    ||          |  |          |             |  ||
     ACGTTATGAGTATGTCGAAGCCTTGTCGGTTCCAGAAATAGATGTTTCAGGGATTGGCCG
1081 ---------+---------+---------+---------+---------+---------+ 1140
     TGCAATACTCATACAGCTTCGGAACAGCCAAGGTCTTTATCTACAAAGTCCCTAACCGGC

                                                    MnlI
                                                  DpnI|
                                              Sau3AI ||
                                        Tth111II   | ||
                                   Fnu4HI      |   | ||
                                  BstAPI|      |   | ||
               CjePI      BbvI    MunI MwoI|      |   | ||
 Tsp509I    MseI    | DrdII |  Tsp509I TseI| AlwI|   | ||
       |       |    |     |  |        |    ||   ||   | ||
     TGGTAATTTATTAAAGTTTTGGTTCGCCCAAGCAATTGCTGCTAACTATGATCCTAAAGA
1141 ---------+---------+---------+---------+---------+---------+ 1200
     ACCATTAAATAATTTCAAAACCAAGCGGGTTCGTTAACGACGATTGATACTAGGATTTCT

                                                             SfaNI
                                   BsrBI                  HinfI|
 CviJI        Tsp509I              AciI |                  TfiI|
      |             |                  | |                    ||
     GGCTAATGGTTTTACAAATTATAAAGGATTTTCCGCTCTATATATGTATGGCATCACAGA
1201 ---------+---------+---------+---------+---------+---------+ 1260
     CCGATTACCAAAATGTTTAATATTTCCTAAAAGGCGAGATATATACATACCGTAGTGTCT
```

FIG. 2E

```
                     AluI
      HaeIV        CviJI     CviJI
      Hin4I  Hpy188IX |    MwoI  |                           BtsI
          |         |   |      |  |                              |
       TTCTCTATCATTCAGAGCTTATGGGGCTTACTCCAAACCAGCAAACGATAAACTCGGCAG
 1261  ---------+---------+---------+---------+---------+---------+ 1320
       AAGAGATAGTAAGTCTCGAATACCCCGAATGAGGTTTGGTCGTTTGCTATTTGAGCCGTC

                            BfaI                      ApoI
                          DpnI |                   Tsp509I
       TspRI Hpy188IX  Sau3AI | |Tsp509I        MseI     | MseI
          |        |        |  | |      |           |      |    |
       TGATTTTACTTTCCGAAAGTTTGATCTAGGTATAATTTCAGCGTTTTAAGTCAAATTTTA
 1321  ---------+---------+---------+---------+---------+---------+ 1380
       ACTAAAATGAAAGGCTTTCAAACTAGATCCATATTAAAGTCGCAAAATTCAGTTTAAAAT

                            Tsp509I
              DraI     Cac8I MseI|          AluI
             MseI|   CviJI | VspI|          CviJI
                 ||      |  |    ||             |
       ATAAAATCTTTAAAAACAGGCTCGCATTAATTATTAGTGAGAGCTTTTTTTTTATTTTTT
 1381  ---------+---------+---------+---------+---------+---------+ 1440
       TATTTTAGAAATTTTTGTCCGAGCGTAATTAATAATCACTCTCGAAAAAAAAATAAAAAA

                                                             ScrFI
                                                            BspGI|
                                                          EcoRII||
                                                          CjePI|||
                                                         AvaII||||
                      CjePI                  MseI      Sau96I||||
                          |                     |            |||||
       ATAATAAAACTAAAAGATTTTTATTATTTTTTGAGTTTTTATGGTTAATCCTATTGGTCC
 1441  ---------+---------+---------+---------+---------+---------+ 1500
       TATTATTTTGATTTTCTAAAAATAATAAAAAACTCAAAAATACCAATTAGGATAACCAGG

                                          FauI
                                         DpnI|
          SfcI                           MnlI|
     AvaII   |                        Sth132I|
   EcoO109I  |                          BglII ||
     Psp5II  |                          BstYI ||
     Sau96I  |                         Sau3AI ||
   Sse8647I  |                     AciI     | ||
          |  |                        |     | ||
       AGGTCCTATAGACGAAACAGAACGCACACCTCCCGCAGATCTTTCTGCTC
 1501  ---------+---------+---------+---------+---------+ 1550
       TCCAGGATATCTGCTTTGTCTTGCGTGTGGAGGGCGTCTAGAAAGACGAG
```

FIG. 2F

CHLAMYDIA ANTIGENS AND CORRESPONDING DNA FRAGMENTS AND USES THEREOF

RELATED U.S. APPLICATION

This present patent application is a Divisional of Ser. No. 09/427,501, filed Oct. 26, 1999, now U.S. Pat. No. 6,403, 101, which claims priority to the following U.S. provisional applications: U.S. Ser. Nos. 60/106,037, filed Oct. 28, 1998 and No. 60/154,658, filed Sep. 20, 1999, each incorporated herein by reference.

FIELD OF THE INVENTION

The present invention relates to Chlamydia antigens and corresponding DNA molecules, which can be used in methods to prevent and treat disease caused by Chlamydia infection in mammals, such as humans.

BACKGROUND OF THE INVENTION

Chlamydiae are prokaryotes. They exhibit morphologic and structural similarities to Gram negative bacteria including a trilaminar outer membrane, which contains lipopolysaccharide and several membrane proteins. Chlamydiae are differentiated from other bacteria by their morphology and by a unique developmental cycle. They are obligate intracellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

Because chlamydiae are small and multiply only within susceptible cells they were long thought to be viruses. However, they have many characteristics in common with other bacteria: (1) they contain both DNA and RNA, (2) they divide by binary fission, (3) their cell envelopes resemble those of other Gram-negative bacteria, (4) they contain ribosomes similar to those of other bacteria, and (5) they are susceptible to various antibiotics. Chlamydiae can be seen in the light microscope, and the genome is about one-third the size of the *Escherichia coli* genome.

Many different strains of chlamydiae have been isolated from birds, man, and other mammals, and these strains can be distinguished on the basis of host range, virulence, pathogenesis, and antigenic composition. There is strong homology of DNA within each species, but surprisingly little between species, suggesting long-standing evolutionary separation.

*C. trachomatis* has a high degree of host specificity, being almost completely limited to man; it causes ocular and genitourinary infections of widely varying severity. In contrast, *C. psittaci* strains are rare in man but are found in a wide range of birds and also in wild, domestic, and laboratory mammals, where they multiply in cells of many organs.

*C. pneumoniae* is a common human pathogen, originally described as the TWAR strain of *C. psittaci*, but subsequently recognized to be a new species. *C. pneumoniae* is antigenically, genetically, and morphologically distinct from other Chlamydia species (*C. trachomatis, C. pecorum* and *C. psittaci*). It shows 10% or less DNA sequence homology with either of *C. trachomatis* or *C. psittaci* and so far appears to consist of only a single strain, TWAR.

*C. pneumoniae* is a common cause of community acquired pneumonia, less frequent only than *Streptococcus pneumoniae* and *Mycoplasma pneumoniae*. Grayston et al., *J. Infect. Dis.* 168: 1231 (1995); Campos et al., *Invest. Ophthalmol. Vis. Sci.* 36: 1477 (1995), each incorporated herein by reference. It can also cause upper respiratory tract symptoms and disease, including bronchitis and sinusitis. See, e.g., Grayston et al., *J. Infect. Dis.* 168: 1231 (1995); Campos et al., *Invest. Ophthalmol. Vis. Sci.* 36: 1477 (1995); Grayston et al., *J. Infect. Dis.* 161: 618 (1990); Marrie, *Clin. Infect. Dis.* 18: 501 (1993). The great majority of the adult population (over 60%) has antibodies to *C. pneumoniae* (Wang et al., *Chlamydial Infections*, Cambridge University Press, Cambridge, p. 329 (1986)), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from formites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, to following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/day, for at least 10 to 14 days). A recently developed drug, azithromycin, is highly effective as a single-dose therapy against chlamydial infections.

In most instances, *C. pneumoniae* infection is mild and without complications, and up to 90% of infections are subacute or unrecognized. Among children in industrialized countries, infections have been thought to be rare up to the age of five years, although a recent study has reported that many children in this age group show PCR evidence of infection despite being seronegative, and estimates a prevalence of 17–19% in 2–4 years old. See, Normann et al., *Acta Paediatrica*, 87: 23–27 (1998). In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 years. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease. See, Saikku et al., *Lancet* 2: 983 (1988); Thom et al., *JAMA* 268: 68 (1992);. Linnanmaki et al., *Circulation* 87: 1030 (1993); Saikku et al., *Annals Int. Med.* 116: 273 (1992); Melnick et al., *Am. J. Med.* 95: 499 (1993). Moreover, the organisms has been detected in atheromas and fatty streaks of the coronary, carotid, peripheral arteries and aorta. See, Shor et al., *South African Med. J.* 82: 158 (1992); Kuo et al., *J. Infect. Dis.* 167: 841 (1993); Kuo et al., *Arteriosclerosis and Thrombosis* 13: 1500 (1993); Campbell et al., *J. Infect. Dis.* 172: 585 (1995); Chiu et al., *Circulation* 96: 2144–2148 (1997). Viable *C. pneumoniae* has been recovered from the coronary and carotid artery. Ramirez et al., *Annals Int. Med.* 125: 979 (1996); Jackson et al., Abst. K121, p272, 36th ICAAC, New Orleans (1996). Furthermore, it has been shown that *C. pneumoniae* can induce changes of atherosclerosis in a rabbit model. See, Fong et al., (1997) *Journal of Clinical Microbiolology* 35: 48. Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbation of asthma in adults, and small-scale studies have shown that prolonged antibiotic treatment was effective at greatly reducing the severity of the disease in some individuals. Hahn et al., *Ann Allergy Asthma Immunol.* 80: 45–49 (1998); Hahn et al., *Epidemiol Infect.* 117: 513–517 (1996); Bjornsson et al., *Scand J. Infect. Dis.* 28: 63–69 (1996); Hahn, *J. Fam. Pract.* 41: 345–351 (1995); Allegra et al., *Eur. Respir. J.* 7: 2165–2168 (1994); Hahn et al., *JAMA* 266: 225–230 (1991).

In light of these results, a protective vaccine against disease caused by *C. pneumoniae* infection would be of considerable importance. There is not yet an effective vaccine for human *C. pneumoniae* infection. Nevertheless, studies with *C. trachomatis* and *C. psittaci* indicate that this is an attainable goal. For example, mice which have recovered from a lung infection with *C. trachomatis* are protected from infertility induced by a subsequent vaginal challenge. Pal et al., *Infection and Immunity* 64: 5341 (1996). Similarly, sheep immunized with inactivated *C. psittaci* were protected from subsequent chlamydial-induced abortions and stillbirths. Jones et al., *Vaccine* 13: 715 (1995). Protection from chlamydial infections has been associated with Th1 immune responses, particularly the induction of INFγ-producing CD4+ T cells. Igietsemes et al., *Immunology* 5: 317 (1993). The adoptive transfer of CD4+ cell lines or clones to nude or SCID mice conferred protection from challenge or cleared chronic disease (Igietseme et al., *Regional Immunology* 5: 317 (1993); Magee et al., *Regional Immunology* 5: 305 (1993)), and in vivo depletion of CD4+ T cells exacerbated disease post-challenge (Landers et al., *Infection & Immunity* 59: 3774 (1991); Magee et al., *Infection & Immunity* 63: 516 (1995)). However, the presence of sufficiently high titres of neutralizing antibody at mucosal surfaces can also exert a protective effect. Cotter et al., *Infection and Immunity* 63: 4704 (1995).

The extent of antigenic variation within the species *C. pneumoniae* is not well characterized. Serovars of *C. trachomatis* are defined on the basis of antigenic variation in major outer membrane proteins (MOMP), but published *C. pneumoniae* MOMP gene sequences show no variation between several diverse isolates of the organism. See, Campbell et al., *Infection and Immunity* 58: 93 (1990); McCafferty et al., *Infection and Immunity* 63: 2387–9 (1995); Knudsen et al., Third Meeting of the European Society for Chlamydia Research, Vienna (1996). Regions of the protein known to be conserved in other chlamydial MOMPs are conserved in *C. pneumoniae*. See, Campbell et al., *Infection and Immunity* 58: 93 (1990); McCafferty et al., *Infection and Immunity* 63: 2387–9 (1995). One study has described a strain of *C. pneumoniae* with a MOMP of greater that usual molecular weight, but the gene for this has not been sequenced. Grayston et al., *J. Infect. Dis.* 168: 1231 (1995). Partial sequences of outer membrane protein 2 from nine diverse isolates were also found to be invariant. Ramirez et al., *Annals Int. Med.* 125: 979 (1996). The genes for HSP60 and HSP70 show little variation from other chlamydial species, as would be expected. The gene encoding a 76 kDa antigen has been cloned from a single strain of *C. pneumoniae*. It has no significant similarity with other known chlamydial genes. Marrie, *Clin. Infect. Dis.* 18: 501 (1993).

Many antigens recognized by immune sera to *C. pneumoniae* are conserved across all chlamydiae, but 98 kDa, 76 kDa and 54 kDa proteins may be *C. pneumoniae*-specific. Campos et al., *Invest. Ophthalmol. Vis. Sci.* 36: 1477 (1995); Marrie, *Clin. Infect. Dis.* 18: 501 (1993); Wiedmann-Al-Ahmad et al., *Clin. Diagn. Lab. Immunol.* 4: 700–704 (1997). Immunoblotting of isolates with sera from patients does show variation of blotting patterns between isolates, indicating that serotypes *C. pneunioniae* may exist. Grayston et al., *J. Infect. Dis.* 168: 1231 (1995); Ramirez et al., *Annals Int. Med.* 125: 979 (1996). However, the results are potentially confounded by the infection status of the patients, since immunoblot profiles of a patient's sera change with time post-infection. An assessment of the number and relative frequency of any serotypes, and the defining antigens, is not yet possible.

Thus, a need remains for effective compositions for preventing, treating, and diagnosing Chlamydia infections.

SUMMARY OF THE INVENTION

In one aspect, the present invention provides purified and isolated DNA molecules that encode Chlamydia which can be used in methods to prevent, treat, and diagnose Chlamydia infection. Encoded polypeptides, designated lorf2, include polypeptides having the amino acid sequence shown in SEQ ID NO: 2 and the DNA molecules include SEQ ID NO: 1 full-length sequence (top sequence) and coding sequence (bottom sequence) for the mature polypeptide. Those skilled in the art will appreciate that the invention also includes DNA molecules that encode mutants, variants, and derivatives of such polypeptides, which result from the addition, deletion, or substitution of non-essential amino acids as described herein. The invention also includes RNA molecules corresponding to the DNA molecules of the invention.

In addition to the DNA and RNA molecules, the invention includes the corresponding polypeptides and monospecific antibodies that specifically bind to such polypeptides.

The present invention has wide application and includes expression cassettes, vectors, and cells transformed or transfected with the polynucleotides of the invention. Accordingly, the present invention provides (i) a method for producing a polypeptide of the invention in a recombinant host system and related expression cassettes, vectors, and transformed or transfected cells; (ii) a live vaccine vectors such as viral or bacterial live vaccine vectors, including, pox virus, alphavirus, *Salmonella typhimurium*, or *Vibrio cholerae* vector, containing a polynucleotide of the invention, such vaccine vectors being useful for, e.g., preventing and treating Chlamydia infection, in combination with a diluent or carrier, and related pharmaceutical compositions and associated therapeutic and/or prophylactic methods; (iii) a therapeutic and/or prophylactic method involving administration of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of Chlamydia in a biological sample, which can involve the use of a DNA or RNA molecule, a monospecific antibody, or a polypeptide of the invention; and (v) a method for purifying a polypeptide of the invention by antibody-based affinity chromatography. The present invention provides purified and isolated DNA molecules, which encode Chlamydia that can be used in methods to prevent, treat, and diagnose Chlamydia infection.

BRIEF DESCRIPTION OF THE DRAWINGS

The present invention will be further understood from the following description with reference to the drawings, in which:

FIGS. 1A–1C shows the nucleotide sequence (top sequence) (SEQ ID NO: 1) and the deduced amino acid sequence (bottom sequence) (SEQ ID NO: 2) of the full-length lorf2 gene from *Chlamydia pneumoniae.*

FIGS. 2A–2F shows the restriction enzyme analysis of nucleotide sequence encoding the *C. pneumoniae* lorf2 gene (SEQ ID NO: 1) and its reverse complement (SEQ ID NO:5).

DETAILED DESCRIPTION OF THE INVENTION

Figure 3:
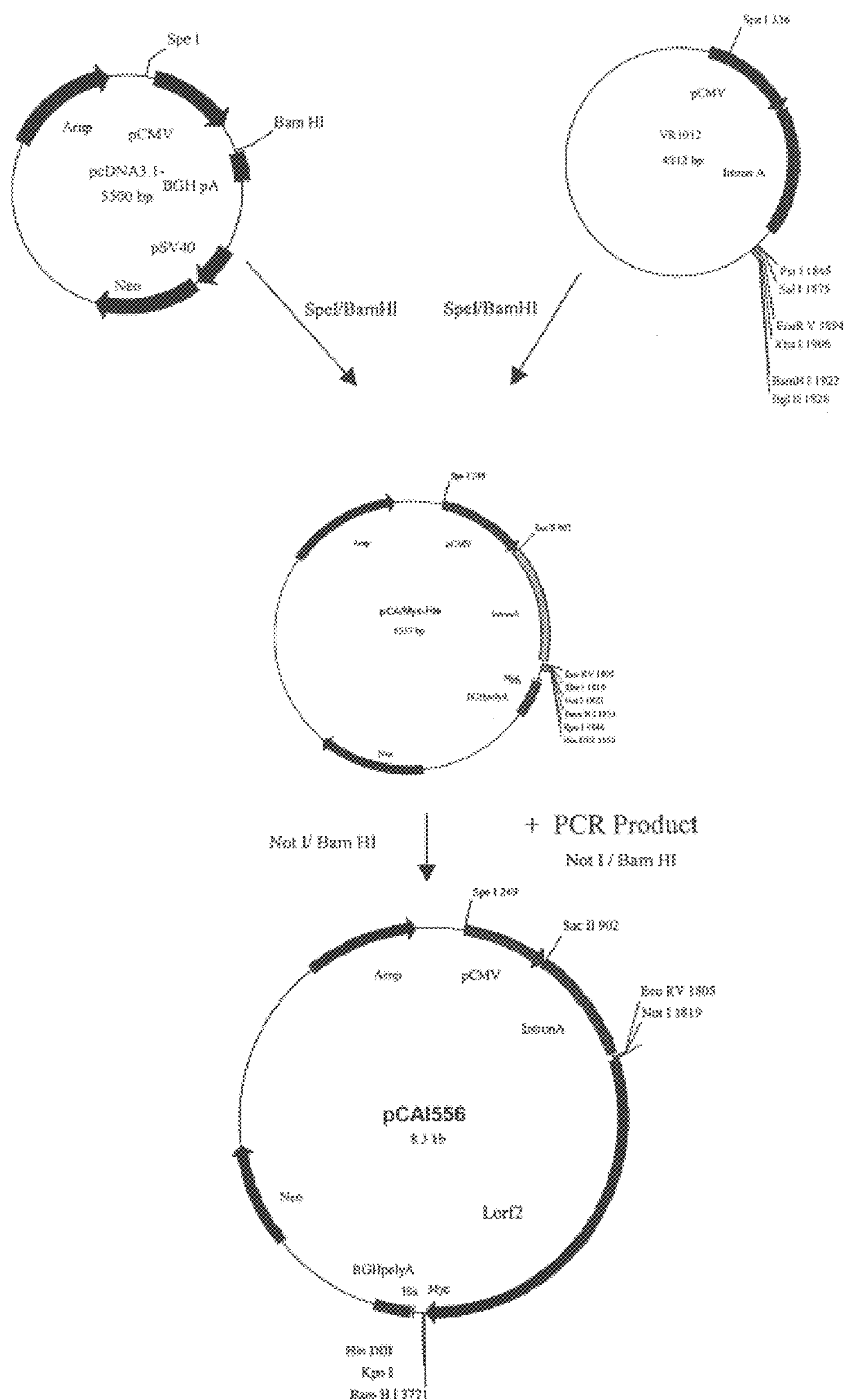
FIG. 3 shows the construction and elements of plasmid pCAI556.

In the *C. pneumoniae* genome, open reading frames (ORFs) encoding chlamydial polypeptides have been identified. These polypeptides include polypeptides permanently found in the bacterial membrane structure, polypeptides that are present in the external vicinity of the bacterial membrane, polypeptides permanently found in the inclusion membrane structure, polypeptides that are present in the external vicinity of the inclusion membrane, and polypeptides that are released into the cytoplasm of the infected cell. These polypeptides can be used in vaccination methods for preventing and treating Chlamydia infection.

According to a first aspect of the invention, there are provided isolated polynucleotides encoding the precursor and mature forms of Chlamydia polypeptides.

An isolated polynucleotide of the invention encodes a polypeptide having an amino acid sequence that is homologous to a Chlamydia amino acid sequence, the Chlamydia amino acid sequence being selected from the group consisting of the amino acid sequences as shown in SEQ ID NOS: 1 and 2. Comparison of the sequence of this gene as to the recently published genome sequence of *C. pneumoniae* reveals that the sequence actually contains at least two open reading frames, a first one in the 5' portion and a second one in the 3' portion of the sequence. Despite the presence of the stop codon at the end of SEQ ID 1*, C. pneumoniae* does make a 76 kDa product. Thus, it appears possible that *C. pneumoniae* is able to read through this stop codon and produce a full length product terminated by the stop codon at the end of the second open reading frame. Furthermore, analysis of the genome sequence indicates that there is at least one in-frame ATG upstream of the start codon. This suggests that the first open reading frame may form part of one or more larger open reading frames. See http://chlamydia-www.berkeley.edu:4231/.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides could be part of a vector or a composition and still be isolated in that such a vector or composition is not part of its natural environment.

A polynucleotide of the invention can be in the form of RNA or DNA (e.g., cDNA, genomic DNA, or synthetic DNA), or modifications or combinations thereof. The DNA can be double-stranded or single-stranded, and, if single-stranded, can be the coding strand or the non-coding (anti-sense) strand. The sequence that encodes a polypeptide of the invention as shown in SEQ ID NO: 1 can be (a) the coding sequence (bottom sequence); (b) a ribonucleotide sequence derived by transcription of (a); or (c) a different coding sequence. This latter, as a result of the redundancy or degeneracy of the genetic code, encodes the same polypeptides as the DNA molecules of which the nucleotide sequences are illustrated in SEQ ID NOS: 1 or2.

By "homologous amino acid sequence" is meant an amino acid sequence that differs from an amino acid sequence shown in SEQ ID NO: 2, only by one or more conservative amino acid substitutions, or by one or more non-conservative amino acid substitutions, deletions, or additions located at positions at which they do not destroy the specific antigenicity of the polypeptide.

Preferably, such a sequence is at least 75%, more preferably 80%, and most preferably 90% identical to an amino acid sequence shown in SEQ ID NO: 2.

Homologous amino acid sequences include sequences that are identical or substantially identical to an amino acid sequence as shown in SEQ ID NO: 2. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

Homology is typically measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Similarity factors include similar size, shape and electrical charge. One particularly preferred method of determining amino acid similarities is the PAM250 matrix described in Dayhoffet et al., 5 *Atlas of Protein Sequence and Structure* 345–352 (1978 & Supp.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the reference sequence. The geometric mean is the square root of the product of these scores. The normalized raw score is the percent homology.

Preferably, a homologous sequence is one that is at least 45%, more preferably 60%, and most preferably 85% identical to the coding sequence of SEQ ID NO: 1.

Polypeptides having a sequence homologous to one of the sequences shown in SEQ ID NOS: 1 and 2, include naturally-occurring allelic variants, as well as mutants and variants or any other non-naturally-occurring variants that are analogous in terms of antigenicity, to a polypeptide having a sequence as shown in SEQ ID NOS: 1 or 2.

An allelic variant is an alternate form of a polypeptide that is characterized as having a substitution, deletion, or addition of one or more amino acids that does not substantially alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., *C. pneumoniae*, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID NOS: 1 and 2. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to any of the sequences shown in SEQ ID NOS: 1 and 2, to the extent that the fragments retain the desired substantial antigenicity of the parent polypeptide (specific antigenicity). Polypeptide derivatives can also be constructed by large internal deletions that remove a substantial part of the parent polypeptide, while retaining the desired specific antigenicity. Generally, polypeptide derivatives should be about at least 12 amino acids in length to maintain the antigenicity. Advantageously, they can be at least 20 amino acids, preferably at least 50 amino acids, more preferably at least 75 amino acids, and most preferably at least 100 amino acids in length.

Useful polypeptide derivatives, e.g., polypeptide fragments, can be designed using computer-assisted analysis of amino acid sequences in order to identify sites in protein antigens having potential as surface-exposed, antigenic regions. Hughes et al., *Infect. Immun.* 60: 3497 (1992).

Polypeptide fragments and polypeptides having large internal deletions can be used for revealing epitopes that are otherwise masked in the parent polypeptide and that may be of importance for inducing, for example, a protective T cell-dependent immune response. Deletions can also remove immunodominant regions of high variability among strains.

It is an accepted practice in the field of immunology to use fragments and variants of protein immunogens as vaccines and immunogens, as all that is required to induce an immune response to a protein may be a small (e.g., 8 to 10 amino acid) region of the protein. This has been done for a number of vaccines against pathogens other than Chlamydia. For example, short synthetic peptides corresponding to surface-exposed antigens of pathogens such as murine mammary tumor virus, peptide containing 11 amino acids (Dion et al., *Virology* 179: 474–477 (1990)); Semliki Forest virus, peptide containing 16 amino acids (Snijders et al., *J. Gen. Virol.* 72: 557–565 (1991)); and canine parvovirus, two overlapping peptides, each containing 15 amino acids (Langeveld et al., *Vaccine* 12: 1473–1480 (1994)) have been shown to be effective vaccine antigens against their respective pathogens.

Polynucleotides encoding polypeptide fragments and polypeptides having large internal deletions can be constructed using standard methods (see, e.g., Ausubel et al., *Current Protocols in Molecular Biology*, John Wiley & Sons Inc. (1994)); for example, by PCR, including inverse PCR, by restriction enzyme treatment of the cloned DNA molecules, or by the method of Kunkel et al. (*Proc. Natl. Acad. Sci. USA* 82: 448 (1985)); biological material available at Stratagene.

A polypeptide derivative can also be produced as a fusion polypeptide that contains a polypeptide or a polypeptide derivative of the invention fused, e.g., at the N- or C-terminal end, to any other polypeptide. For construction of DNA encoding the amino acid sequence corresponding to hybrid fusion proteins, a first DNA encoding amino acid sequence corresponding to portions of SEQ ID NO: 1 or 2 is joined to a second DNA using methods described in, for example, U.S. Pat. No. 5,844,095, incorporated herein by reference. A product can then be easily obtained by translation of the genetic fusion. Vectors for expressing fusion polypeptides are commercially available, such as the pMal-c2 or pMal-p2 systems of New England Biolabs, in which the fusion peptide is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in the invention includes a polypeptide or polypeptide derivative of the invention fused to a polypeptide having adjuvant activity, such as, e.g., the subunit B of either cholera toxin or *E. coli* heat-labile toxin. Several possibilities are can be used for achieving fusion. First, the polypeptide of the invention can be fused to the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID NO: 1. Hybridization procedures are described in, e.g., Ausubel et al., *Current Protocols in Molecular Biology*, John Wiley & Sons Inc. (1994); Silhavy et al., *Experiments With Gene Fusions*, Cold Spring Harbor Laboratory Press (1984); Davis et al., *A Manual for Genetic Engineering: Advanced Bacterial Genetics*, Cold Spring Harbor Laboratory Press (1980), each incorporated herein by reference. Important parameters that can be considered for optimizing hybridization conditions are reflected in a formula that allows calculation of a critical value, the melting temperature above which two complementary DNA strands separate from each other. Casey and Davidson, *Nucl. Acid Res.* 4: 1539 (1977). This formula is as follows:

$$Tm=81.5+0.5\times(\%G+C)+1.6\log(\text{positive ion concentration})-0.6\times(\%\text{ formamide}).$$

Under appropriate stringency conditions, hybridization temperature (Th) is approximately 20–40° C., 20–25° C. or, preferably, 30–40° C. below the calculated Tm. Those skilled in the art will understand that optimal temperature and salt conditions can be readily determined empirically in preliminary experiments using conventional procedures.

For example, stringent conditions can be achieved, both for pre-hybridizing and hybridizing incubations, (i) within 4–16 hours at 42° C., in 6×SSC containing 50% formamide or (ii) within 4–16 hours at 65° C. in an aqueous 6×SSC solution (1 M NaCl, 0.1 M sodium citrate (pH 7.0)).

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20–30 bases do not exactly follow the rules set forth above. In such cases, the formula for calculating the Tm is as follows:

$$Tm=4\times(G+C)+2(A+T).$$

For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the encoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can overexpress a polynucleotide of the invention or express it in a modified, mutated form, such as a non-toxic form, if appropriate. For vaccine compositions and uses of the proteins and peptides and encoding nucleotides of the present invention for protection against diseases caused by Chlamydia, it is not preferred to use naked DNA encoding the protein or peptides and administering these nucleotides intranasally or intramuscularly. For these proteins, it is preferred to administer the encoding nucleic acids by other routes such as intradermally and/or to formulate the encoding nucleic acids to improve (or adjuvant) the immune response. It is also preferred to include the encoding nucleic acid as part of a recombinant live vector, such as a viral or bacterial vector for use as the immunizing agent. It is also preferred to immunize with vaccine formulations comprising the proteins or peptides of the invention themselves. These vaccine formulations may include the use of adjuvants.

According to a second aspect of the invention, there is therefore provided (i) an expression cassette containing a DNA molecule of the invention placed under the control of the elements required for expression, in particular under the control of an appropriate promoter; (ii) an expression vector containing an expression cassette of the invention; (iii) a prokaryotic or eukaryotic cell transformed or transfected with an expression cassette and/or vector of the invention, as well as (iv) a process for producing a polypeptide or polypeptide derivative encoded by a polynucleotide of the invention, which involves culturing a prokaryotic or eukaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from prokaryotic and eukaryotic hosts. Eukaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. Preferably, a prokaryotic host such as *E. coli* is used. Bacterial and eukaryotic cells are available from a number of different sources to those skilled in the art, e.g., the American Type Culture Collection (ATCC; Rockville, Md.).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding regions are widely known and available to those skilled in the art and includes, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., *Protein Engineering* 4: 843 (199 1)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide (Takase et al., *J. Bact*. 169: 5692 (1987)).

The expression cassette is typically part of an expression vector, which is selected for its ability to replicate in the chosen expression system. Expression vectors (e.g., plasmids or viral vectors) can be chosen from those described in Pouwels et al. (*Cloning Vectors: Laboratory Manual*, 85, Supp. 1987). They can be purchased from various commercial sources.

Methods for transforming/transfecting host cells with expression vectors will depend on the host system selected as described in Ausubel et al., *Current Protocols in Molecular Biology*, John Wiley & Sons Inc. (1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supernatant after centrifugation of the recombinant cell culture. Typically, the recombinant polypeptide can be purified by antibody-based affinity purification or by any other method that can be readily adapted by a person skilled in the art, such as by genetic fusion to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be useful in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in a third aspect of the invention, there is provided (i) a vaccine vector such as a poxvirus, containing a DNA molecule of the invention, placed under the control of elements required for expression; (ii) a composition of matter containing a vaccine vector of the invention, together with a diluent or carrier; particularly, (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia; and particularly, (v) a method for preventing and/or treating a Chlamydia (e.g., *C. trachomatis, C. psittaci, C. pneumonia, C. pecorum*) infection, which involves administering a prophylactic or therapeutic amount of a vaccine vector of the invention to an individual in need. Additionally, the third aspect of the invention encompasses the use of a vaccine vector of the invention in the preparation of a medicament for preventing and/or treating Chlamydia infection.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), that enhances the immune response (adjuvant effect). Thus, a vaccine vector can include an additional DNA sequence encoding, e.g., a chlamydial antigen , or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof; or a cytokine such as IL-2 or IL-12.

In vaccination methods for treating or preventing infection in a mammal, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses, alphavirus, and poxviruses as well as bacterial vectors, e.g., Shigella, Salmonella, *Vibrio cholerae*, Lactobacillus, Bacille bilié de Calmette-Guérin (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. No. 4,722,848 and U.S. Pat. No. 5,364,773, respectively (also see, e.g., Tartaglia et al., *Virology* 188: 217 (1992)) for a description of a vaccinia virus vector; and Taylor et al, *Vaccine* 13: 539 (1995) for a reference of a canary pox). Poxvirus vectors capable of expressing a polynucleotide of the invention can be obtained by homologous recombination as described in Kieny et al., *Nature* 312: 163 (1984) so that the polynucleotide of the invention is inserted in the viral genome under appropriate conditions for expression in mammalian cells. Generally, the dose of vaccine viral vector, for therapeutic or prophylactic use, can be of from about $1\times10^4$ to about $1\times10^{11}$ advantageously from about $1\times10^7$ to about $1\times10^{10}$, preferably of from about $1\times10^7$ to about $1\times10^9$ plaque-forming units per kilogram. Preferably, viral vectors are administered parenterally; for example, in three doses, four weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in Mekalanos et al., *Nature* 306: 551 (1983) and U.S. Pat. No. 4,882,278 (strain in which a substantial amount of the coding sequence of each of the two ctxA alleles has been deleted so that no functional cholerae toxin is produced); WO 92/11354 (strain in which the irgA locus is inactivated by mutation; this mutation can be combined in a single strain with ctxA mutations); and WO 94/1533 (deletion mutant lacking functional ctxA and attRS1 DNA sequences). These strains can be genetically engineered to express heterologous antigens, as described in WO 94/19482. An effective vaccine dose of a *Vibrio cholerae* strain capable of expressing a polypeptide or polypeptide derivative encoded by a DNA molecule of the. invention can contain, e.g., about $1\times10^5$ to about $1\times10^9$, preferably about $1\times10^6$ to about $1\times10^8$ viable bacteria in an appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al., *Bio/Technology* 6: 693 (1988) and WO 92/11361. Preferred routes of administration include all mucosal routes; most preferably, these vectors are administered intranasally or orally.

Others bacterial strains useful as vaccine vectors are described in High et al., *EMBO* 11: 1991 (1992); Sizemore et al., *Science* 270: 299 (1995) (Shigella flexneri); Medaglini et al., *Proc. Natl. Acad. Sci. USA* 92: 6868 (1995) (*Streptococcus gordonii*); and Flynn, *Cell. Mol. Biol.* 40: 31 (1994), WO 88/6626, WO 90/0594, WO 91/13157, WO 92/1796, and WO 92/21376 (Bacille Calmette Guerin).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to a fourth aspect of the invention, there is also provided (i) a composition of matter containing a polynucleotide of the invention, together with a diluent or carrier; (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomatis, C. psittaci, C. pneumoniae*, or *C. pecorum*) infection, by administering a prophylactic or therapeutic amount of a polynucleotide of the invention to an individual in need. Additionally, the fourth aspect of the invention encompasses the use of a polynucleotide of the invention in the preparation of a medicament for preventing and/or treating Chlamydia infection. The fourth aspect of the invention preferably includes the use of a DNA molecule placed under conditions for expression in a mammalian cell, e.g., in a plasmid that is unable to replicate in mammalian cells and to substantially integrate in a mammalian genome.

Polynucleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, *Molec. Cell Biol.* 5: 281(1985)). The desmin promoter (Li et al., *Gene* 78: 243 (1989), Li & Paulin, *J. Biol. Chem.* 266: 6562 (1991), and Li & Paulin, *J. Biol. Chem.* 268: 10403 (1993)) is tissue-specific and drives expression in muscle cells. More generally, useful vectors are described, i.a., WO 94/21797 and Hartikka et al., *Human Gene Therapy* 7: 1205 (1996).

For DNA/RNA vaccination, the polynucleotide of the invention can encode a precursor or a mature form. When it encodes a precursor form, the precursor form can be homologous or heterologous. In the latter case, a eukaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen or a fragment, derivative, mutant, or analog thereof. A polynucleotide encoding a cytokine, such as interleukin-2 (IL-2) or interleukin-12 (IL-12), can also be added to the composition so that the immune response is enhanced. These additional polynucleotides are placed under appropriate control for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, microparticles, e.g., gold microparticles, precipitating agents, e.g., calcium phosphate, or any other transfection-facilitating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake. It can be, i.a., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liposomes are well-known in the art (see, e.g., *Liposomes: A Practical Approach*, RPC New Ed, IRL press (1990)), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy) propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in, e.g., WO 90/11092.

Other transfection-facilitating compounds can be added to a formulation containing cationic liposomes. A number of them are described in, e.g., WO 93/18759, WO 93/19768, WO 94/25608, and WO 95/2397. They include, i.a., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and Tang et al. (*Nature* 356: 152 (1992)). In this case, the microparticle-coated polynucleotides can be injected via intradermal or intra-epidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 mg to about 1 $\mu$g, preferably, from about 10 $\mu$g to about 800 $\mu$g and, more preferably, from about 25 $\mu$g to about 250 $\mu$g, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intra-epidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a fifth aspect of the invention, there is provided a nucleotide probe or primer having a sequence found in or derived by degeneracy of the genetic code from a sequence shown in SEQ ID NO: 1.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID NOS: 1 and 2, or to a complementary or anti-sense sequence. Generally, probes are significantly shorter than full-length sequences shown in SEQ ID NOS: 1 and 2; for example, they can contain from about 5 to about 100, preferably from about 10 to about 80 nucleotides. In particular, probes have sequences that are at least 75%, preferably at least 85%, more preferably 95% homologous to a portion of a sequence as shown in SEQ ID NOS: 1 and 2 or that are complementary to such sequences. Probes can contain modified bases such as inosine, methyl-5-deoxycytidine, deoxyuridine, dimethylamino-5-deoxyuridine, or diamino-2,6-purine. Sugar or phosphate residues can also be modified or substituted. For example, a deoxyribose residue can be replaced by a polyamide (Nielsen et al., *Science* 254: 1497 (1991)) and phosphate residues can be replaced by ester groups such as diphosphate, alkyl, arylphosphonate and phosphorothioate esters. In addition, the 2'-hydroxyl group on ribonucleotides can be modified by including, e.g., alkyl groups.

Probes of the invention can be used in diagnostic tests, as capture or detection probes. Such capture probes can be conventionally immobilized on a solid support, directly or indirectly, by covalent means or by passive adsorption. A detection probe can be labelled by a detection marker selected from radioactive isotopes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., *Molecular Cloning: A Laboratory Manual* (1982) Cold Spring Harbor Laboratory Press, Cold Spring Harbor, N.Y.), Southern blot (*Southern, J. Mol. Biol.* 98: 503 (1975)), northern blot (identical to Southern blot to the exception that RNA is used as a target), or the sandwich technique (Dunn et al., *Cell* 12: 23 (1977)). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers can be labelled.

Thus, the invention also encompasses (i) a reagent containing a probe of the invention for detecting and/or identifying the presence of Chlamydia in a biological material; (ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifyng the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, a sixth aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID NOS: 1 and 2. Briefly, a monospecific hyperimmune antiserum can be raised against a purified reference polypeptide as such or as a fusion polypeptide, for example, an expression product of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (Towbin et al., *Proc. Natl. Acad. Sci. USA* 76: 4350 (1979)), dot blot, and ELISA, as described below.

In a Western blot assay, the product to be screened, either as a purified preparation or a total *E. coli* extract, is submitted to SDS-Page electrophoresis as described by Laemmli, *Nature* 227: 680 (1970). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 $\mu$l of a preparation at about 10 $\mu$g protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 $\mu$l PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 $\mu$l of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 $\mu$g/ml is serially two-fold diluted in 50 mM Tris-HCl (pH 7.5). 100 $\mu$l of each dilution are applied to a nitrocellulose membrane 0.45 $\mu$m set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to a seventh aspect of the invention, there is provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia; and particularly, (iv) a method for preventing and/or treating a Chlamydia (e.g., *C. trachomatis. C. psittaci, C. pneumoniae*, or *C. pecorum*) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the subcutaneous or intramuscular route is most preferred. The choice can also depend upon the nature of the vaccine agent. For example, a polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see *Liposomes: A Practical Approach* (supra).

Adjuvants other than liposomes and the like can also be used and are known in the art. An appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 $\mu$g to about 500 mg, preferably from about 1 mg to about 200 mg. For the parenteral route of administration, the dose usually should not exceed about 1 mg, preferably about 100 $\mu$g.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., *Current Protocols in Immunology* (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, a ninth aspect of the invention provides (i) a reagent for detecting the presence of Chlamydia in a biological sample that contains an antibody, polypeptide, or lo polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chlamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a tenth aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., *Antibodies: A Laboratory Manual*, D. Lane, E. Harlow, Eds. (1988).

Briefly, a biological sample, such as an *C. pneumoniae* extract, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An antibody of the invention can be screened for therapeutic efficacy as described as follows. According to an eleventh aspect of the invention, there is provided: (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., *C. trachomatis, C. psittaci, C. pneumoniae* or *C. pecorum*) infection, by administering a therapeutic or prophylactic amount of a monospecific antibody of the invention to an individual in need. Additionally, the eleventh aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the *C. pneumoniae* mouse model. Those skilled in the art will recognize that the *C. pneumoniae* strain of the model can be replaced with another Chlamydia strain. For example, the efficacy of DNA molecules and polypeptides from *C. pneumoniae* is preferably evaluated in a mouse model using an *C. pneumoniae* strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the *E. coli* heat-labile toxin (LT), the *Clostridium difficile* toxin A and the *pertussis* toxin (PT), or combinations, subunits, toxoids, or mutants thereof For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant).

Additional LT mutants that can be used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli*, Salmonella minnesota, Salmonella typhimurium, or *Shigella flexneri*; saponins, or polylactide glycolide (PLGA) microspheres, can also be used in mucosal administration.

Adjuvants usefuil for both mucosal and parenteral administrations include polyphosphazene (WO 95/2415), DC-chol (3 b-(N-(N',N'-dimethyl aminomethane)-carbamoyl) cholesterol (U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in Remington's Pharmaceutical Sciences, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids. In addition, compounds containing more than one of the above-listed components coupled together, can be used. The invention also includes compositions for carrying out these methods, i.e., compositions containing a Chlamydia antigen (or antigens) of the invention, an adjuvant, and one or more of the above-listed compounds, in a pharmaceutically acceptable carrier or diluent.

Amounts of the above-listed compounds used in the methods and compositions of the invention can readily be determined by one skilled in the art. In addition, one skilled in the art can readily design treatment/immunization schedules. For example, the non-vaccine components can be administered on days 1–14, and the vaccine antigen+adjuvant can be administered on days 7, 14, 21, and 28.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation. Polypeptides having a sequence homologous to one of the sequences shown in SEQ ID NOS: 1 and 2, include naturally-occurring allelic variants, as well as mutants or any other non-naturally occurring variants that are analogous in terms of antigenicity, to a polypeptide.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., *C. pneumoniae*, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID NOS: 1 and 2. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to any of the sequences shown in SEQ ID NO: 1, to the extent that the fragments retain the substantial antigenicity of the parent polypeptide (specific antigenicity). Polypeptide derivatives can also be constructed by large internal deletions that remove a substantial part of the parent polypeptide, while retaining specific antigenicity. Generally, polypeptide derivatives should be about at least 12 amino acids in length to maintain antigenicity. Advantageously, they can be at least 20 amino acids, preferably at least 50 amino acids, more preferably at least 75 amino acids, and most preferably at least 100 amino acids in length. Useful polypeptide derivatives, e.g., polypeptide fragments, can be designed using computer-assisted analysis of amino acid sequences in order to identify sites in protein antigens having potential as surface-exposed, antigenic regions. See e.g., Hughes et al., *Infect. Immun.* 60: 3497 (1992).

Polypeptide fragments and polypeptides having large internal deletions can be used for revealing epitopes that are otherwise masked in the parent polypeptide and that may be of importance for inducing a protective T cell-dependent immune response. Deletions can also remove immunodominant regions of high variability among strains.

It is an accepted practice in the field of immunology to use fragments and variants of protein immunogens as vaccines, as all that is required to induce an immune response to a protein is a small (e.g., 8 to 10 amino acid) immunogenic region of the protein. This has been done for a number of vaccines against pathogens other than Chlamydia. For example, short synthetic peptides corresponding to surface-exposed antigens of pathogens such as murine mammary tumor virus, peptide containing 11 amino acids; (see e.g., Dion et al., *Virology* 179: 474–477 (1990)) Semliki Forest virus, peptide containing 16 amino acids (see e.g., Snijders et al., *J. Gen. Virol.* 72: 557–565 (1991)), and canine parvovirus, 2 overlapping peptides, each containing 15 amino acids (see e.g., Langeveld et al. *Vaccine* 12: 1473–1480 (1994)), have been shown to be effective vaccine antigens against their respective pathogens.

Polynucleotides encoding polypeptide fragments and polypeptides having large internal deletions can be constructed using standard methods, for example, by PCR, including inverse PCR, by restriction enzyme treatment of the cloned DNA molecules, or. by the method of Kunkel et al. (*Proc. Natl. Acad. Sci. USA* 82:448 (1985)) using biological material available at Stratagene.

A polypeptide derivative can also be produced as a fusion polypeptide that contains a polypeptide or a polypeptide derivative of the invention fused, e.g., at the N- or C-terminal end, to any other polypeptide (hereinafter referred to as a peptide tail). Such a product can be easily obtained by translation of a genetic fusion, i.e., a hybrid gene. Vectors for expressing fusion polypeptides are commercially available, such as the pMal-c2 or pMal-p2 systems of New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in invention includes a polypeptide or polypeptide derivative of the invention fused to a polypeptide having adjuvant activity, such as, e.g., subunit B of either cholera toxin or *E. coli* heat-labile toxin. Several possibilities are can be used for achieving fusion. First, the polypeptide of the invention can be fused to the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID NOS: 1 or 2. Hybridization procedures are, described in e.g., Ausubel et al., *Current Protocols in Molecular Biology*, John Wiley & Sons Inc. (1994), Silhavy et al. *Experiments With Genetic Fusions*, Cold Spring Harbor Laboratory Press (1984); Davis et al., *A Manual for Genetic Engineering: Advanced Bacterial Genetics*, Cold Spring Harbor Laboratory Press (1980). Important parameters that can be considered for optimizing hybridization conditions are reflected in a formula that allows calculation of a critical value, the melting temperature above which two complementary DNA strands separate from each other. Casey and Davidson, *Nucl. Acid Res.* 4: 1539 (1977). This formula is as follows: Tm=81.5+0.41×(% G+C)+16.6 log (cation ion concentration)−0.63×(% formamide)−600/base number. Under appropriate stringency conditions, hybridization temperature (Th) is approximately 20–40° C., 20–25° C., or, preferably 30–40° C. below the calculated Tm. Those skilled in the art will understand that optimal temperature and salt conditions can be readily determined empirically in preliminary experiments using conventional procedures.

For example, stringent conditions can be achieved, both for pre-hybridizing and hybridizing incubations, (i) within 4–16 hours at 42° C., in 6×SSC containing 50% formamide or (ii) within 4–16 hours at 65° C. in an aqueous 6×SSC solution (1 M NaCl, 0.1 M sodium citrate (pH 7.0)). Typically, hybridization experiments are performed at a temperature from 60 to 68° C., e.g., 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20–30 bases do not exactly follow the rules set forth above. In such cases, the formula for calculating the Tm is as follows: Tm=4×(G+C)+2(A+T). For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the dncoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can over-express a polynucleotide of the invention or express it in a non-toxic, mutated form.

According to a second aspect of the invention, there is therefore provided (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from procaryotic and eucaryotic hosts. Eucaryotic hosts include yeast cells (e.g., *Saccharomyces cerevisiae* or *Pichia pastoris*), mammalian cells (e.g., COS 1, NIH3T3, or JEG3 cells), arthropods cells (e.g., *Spodoptera frugiperda* (SF9) cells), and plant cells. Preferably, a procaryotic host such as *E. coli* is used. Bacterial and eucaryotic cells are available from a number of different sources to those skilled in the art, e.g., the American Type Culture Collection (ATCC; Rockville, Md.).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide-encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding loregions are widely known and available to those skilled in the art and includes, for example, the promoter of *Salmonella typhimuriun* (and derivatives) that is inducible by arabinose (promoter araB) and is functional in Gram-negative bacteria such as *E. coli* (as described in U.S. Pat. No. 5,028,530 and in Cagnon et al., *Protein Engineering* 4: 843 (1991); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide. See Takase et al., *J. Bact.* 169: 5692 (1987).

The expression cassette is typically part of an expression vector, which is selected for its ability to replicate in the chosen expression system. Expression vectors (e.g., plasmids or viral vectors) can be chosen from those described in Pouwels et al. (Cloning Vectors: A Laboratory Manual 1985, Suppl. 1987). They can be purchased from various commercial sources.

Methods for transforming/transfecting host cells with expression vectors will depend on the host system selected as described in Ausubel et al., *Current Protocols in Molecular Biology*, John Wiley & Sons Inc. (1994)).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supematant after centriftigation of the recombinant cell culture. Typically, the recombinant polypeptide can be purified by antibody-based affinity purification or by any other method that can be readily adapted by a person skilled in the art, such as by genetic fuision to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be usefuil in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in a third aspect of the invention, there is provided (i) a vaccine vector such as a poxvirus, containing a DNA molecule of the invention, placed under the control of elements required for expression; (ii) a composition of matter containing a vaccine vector of the invention, together with a diluent or carrier; particularly, (iii) a pharmaceutical composition containing a therapeutically or prophylactically effective amount of a vaccine vector of the invention; (iv) a method for inducing an immune response against Chlamydia in a mammal (e.g., a human; altematively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia; and particularly, (v) a method for preventing and/or treating a Chlamydia (e.g., *C. trachomatis, C. psittaci, C. pneumoniae, C. pecorum*) infection, which involves administering a prophylactic or therapeutic amount of a vaccine vector of the invention to an individual in need. Additionally, the third aspect of the invention encompasses the use of a vaccine vector of the invention in the preparation of a medicament for preventing and/or treating Chlamydia infection.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), which enhances the immune response (adjuvant effect). Thus, a vaccine vector can include an additional DNA sequence encoding, e.g., a chlamydial antigen, or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof, or a cytokine such as IL-2 or IL-12.

In vaccination methods for treating or preventing infection in a mammal, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., Shigella, Salmonella, *Vibrio cholerae*, Lactobacillus, Bacille bilié de Calmette-Guérin (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. No. 4,722,848 and U.S. Pat. No. 5,364,773, respectively (also see, e.g., Tartaglia et al., Virology (1992) 188:217) for a description of a vaccinia virus vector; and Taylor et al, Vaccine (1995) 13:539 for a reference of a canary pox). Poxvirus vectors capable of expressing a polynucleotide of the invention can be obtained by homologous recombination as described in Kieny et al., Nature (1984) 312:163 so that the polynucleotide of the invention is inserted in the viral genome under appropriate conditions for expression in mammalian cells. Generally, the dose of vaccine viral vector, for therapeutic or prophylactic use, can be of from about $1\times10^4$ to about $1\times10^{11}$, advantageously from about $1\times10^7$ to about $1\times10^{10}$, preferably of from about $1\times10^7$ to about $1\times10^9$ plaque-forming units per kilogram. Preferably, viral vectors are administered parenterally; for example, in 3 doses, 4 weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in Mekalanos et al., Nature (1983) 306:551 and U.S. Pat. No. 4,882,278 (strain in which a substantial amount of the coding sequence of each of the two ctxA alleles has been deleted so that no functional cholerae toxin is produced); WO 92/11354 (strain in which the irgA locus is inactivated by mutation; this mutation can be combined in a single strain with ctxA mutations); and WO 94/1533 (deletion mutant lacking functional ctxA and attRS1 DNA sequences). These strains can be genetically engineered to express heterologous antigens, as described in WO 94/19482. An effective vaccine dose of a *Vibrio cholerae* strain capable of expressing a polypeptide or polypeptide derivative encoded by a DNA molecule of the invention can contain, e.g., about $1\times10^5$ to about $1\times10^9$, preferably about $1\times10^6$ to about $1\times10^8$ viable bacteria in an appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al. (Bio/Technology (1988) 6:693) and WO 92/11361. Preferred routes of administration include all mucosal routes; most preferably, these vectors are administered intranasally or orally.

Others bacterial strains useful as vaccine vectors are described in High et al., EMBO (1992) 11:1991 and Sizemore et al., Science (1995) 270:299 (*Shigella flexneri*); Medaglini et al., Proc. Natl. Acad. Sci. USA (1995) 92:6868 (*Streptococcus gordonii*); and Flynn J. L., Cell. Mol. Biol. (1994) 40 (suppl. I):31, WO 88/6626, WO 90/0594, WO 91/13157, WO 92/1796, and WO 92/21376 (Bacille Calmette Guerin).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to a fourth aspect of the invention, there is also provided (i) a composition of matter containing a polynucleotide of the invention, together with a diluent or carrier; (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomatis, C. psittaci, C. pneumoniae*, or *C. pecorum*) infection, by administering a prophylactic or therapeutic amount of a polynucleotide of the invention to an individual in need. Additionally, the fourth aspect of the invention encompasses the use of a polynucleotide of the invention in the preparation of a medicament for preventing and/or treating Chlamydia infection. The fourth aspect of the invention preferably includes the use of a DNA molecule placed under conditions for expression in a mammalian cell, e.g., in a plasmid that is unable to replicate in mammalian cells and to substantially integrate in a mammalian genome.

Polynucleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, *Molec. Cell Biol*. 5:281 (1985)). The desmin promoter (Li et al., *Gene* 78: 243 (1989); Li & Paulin, *J. Biol, Chem*. 266: 6562 (1991); and Li & Paulin, *J. Biol. Chem*. 268: 10403 (1993)) is tissue-specific and drives expression in muscle cells. More generally, useful vectors are described, i.a., WO 94/21797 and Hartikka et al., *Human Gene Therapy* 7: 1205 (1996).

For DNA/RNA vaccination, the polynucleotide of the invention can encode a precursor or a mature form. When it encodes a precursor form, the precursor form can be homologous or heterologous. In the latter case, a eucaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen such as urease subunit A, B, or both; or a fragment, derivative, mutant, or analog thereof. A polynucleotide encoding a cytokine, such as interleukin-2 (IL-2) or interleukin-12 (IL-12), can also be added to the composition so that the immune response is enhanced. These additional polynucleotides are placed under appropriate control-for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, microparticles, e.g., gold microparticles, precipitating agents, e.g., calcium phosphate, or any other transfection-facilitating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake. It can be, i.a., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liposomes are well known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy) propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as, for example, described in WO 90/11092.

Other transfection-facilitating compounds can be added to a formulation containing cationic liposomes. A number of them are described in, e.g., WO 93/18759, WO 93/19768, WO 94/25608, and WO 95/2397. They include, i.a., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and Tang et al. (Nature 356: 152 (1992)). In this case, the microparticle-coated polynucleotides can be injected via intradeimal or intra-epidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 μg to about 1 mg, preferably, from about 10 μg to about 800 μg and, more preferably, from about 25 μg to about 250 μg, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a fifth aspect of the invention, there is provided a nucleotide probe or primer having a sequence found in or derived by degeneracy of the genetic code from a sequence shown in SEQ ID NOS: 1 or 2.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID NOS: 1 and 2, or to a complementary or anti-sense sequence. Generally, probes are significantly shorter than full-length sequences shown in SEQ ID NOS: 1 and 2; for example, they can contain from about 5 to about 100, preferably from about 10 to about 80 nucleotides. In particular, probes have sequences that are at least 75%, preferably at least 85%, more preferably 95% homologous to a portion of a sequence as shown in SEQ ID NOS: 1 and 2 or that are complementary to such sequences. Probes can contain modified bases such as inosine, methyl-5-deoxycytidine, deoxyuridine, dimethylamino-5-deoxyuridine, or diamino-2, 6-purine. Sugar or phosphate residues can also be modified or substituted. For example, a deoxyribose residue can be replaced by a polyamide (Nielsen et al., Science (1991) 254:1497) and phosphate residues can be replaced by ester groups such as diphosphate, alkyl, arylphosphonate and phosphorothioate esters. In addition, the 2'-hydroxyl group on ribonucleotides can be modified by including, e.g., alkyl groups.

Probes of the invention can.be used in diagnostic tests, as capture or detection probes. Such capture probes can be conventionally immobilized on a solid support, directly or indirectly, by covalent means or by passive adsorption. A detection probe can be labelled by a detection marker selected from radioactive isotopes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, *J. Mol. Biol.* (1975) 98:503), northern blot (identical to Southern blot to the exception that RNA is used as a target), or the sandwich technique (Dunn et al., *Cell* 12: 23 (1977)). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers. can be labelled.

Thus, the invention also encompasses (i) a reagent containing a probe of the invention for detecting and/or identifying the presence of Chlamydia in a biological material; (ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, a sixth aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID NO: 2. Briefly, a monospecific hyperimmune antiserum can be raised against a purified reference polypeptide as such or as a fusion polypeptide, for example, an expression product of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (Towbin et al., *Proc. Natl. Acad. Sci. USA* 76: 4350 (1979)), dot blot, and ELISA, as described below.

In a Western blot assay, the product to be screened, either as a purified preparation or a total *E. coli* extract, is submitted to SDS-Page electrophoresis as described by Laemmli (*Nature* 227: 680 (1970)). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 μl of a preparation at about 10 μg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 μl PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 μl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non-immune control serum.

In a dot blot assay, a purified product is preferred, although a whole cell extract can also be used. Briefly, a solution of the product at about 100 μg/ml is serially two-fold diluted in 50 mM Tris-HCl (pH 7.5). 100 μl of each dilution are applied to a nitrocellulose membrane 0.45 μm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to a seventh aspect of the invention, there is provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia; and particularly, (iv) a method for preventing and/or treating a Chlamydia (e.g., *C. trachomatis. C. psittaci, C. pneumotiiae*, or *C. pecorum*) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric; intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the sub-cutaneous or intramuscular route is most preferred. The choice can also depend upon the nature of the vaccine agent. For example, a polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragrment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach (supra).

Adjuvants other than liposomes and the like can also be used and are known in the art. An appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 $\mu$g to about 500 mg, preferably from about 1 mg to about 200 mg. For the parenteral route of administration, the dose usually should not exceed about 1 mg, preferably about 100 $\mu$g.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, a ninth aspect of the invention provides (i) a reagent for detecting the presence of Chlamydia in a biological sample that contains an antibody, polypeptide, or polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chlamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a tenth aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., Antibodies: A Laboratory Manual, D. Lane, E. Harlow, Eds. (1988).

Briefly, a biological sample, such as an *C. pneumoniae* extract, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An antibody of the invention can be screened for therapeutic efficacy as described as follows. According to an eleventh aspect of the invention, there is provided (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., *C. trachomatis, C. psittaci, C. pneumoniae* or *C. pecorum*) infection, by administering a therapeutic or prophylactic amount of a monospecific antibody of the invention to an individual in need. Additionally, the eleventh aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the *C. pneumoniae* mouse model . Those skilled in the art will recognize that the *C. pneumoniae* strain of the model can be replaced with another Chlamydia strain. For example, the efficacy of DNA molecules and polypeptides from *C. pneumoniae* is preferably evaluated in a mouse model using an *C. pneumoniae* strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the *E. coli* heat-labile toxin (LT), the *Clostridium difficile* toxin A and the *pertussis* toxin (PT), or combinations, subunits, toxoids, or mutants thereof. For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli*, Salmonella minnesota, Salmonella typhimurium, or *Shigella flexneri*; saponins, or polylactide glycolide (PLGA) microspheres, can also be used in mucosal administration.

Adjuvants useful for both mucosal and parenteral administrations include polyphosphazene (WO 95/2415), DC-chol (3 b-(N-(N',N'-dimethyl aminomethane)-carbamoyl) cholesterol; U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids. In addition, compounds containing more than one of the above-listed components coupled together, can be used. The invention also includes compositions for carrying out these methods, i.e., compositions containing a Chlamydia antigen (or antigens) of the invention, an adjuvant, and one or more of the above-listed compounds, in a pharmaceutically acceptable carrier or diluent.

Amounts of the above-listed compounds used in the methods and compositions of the invention can readily be determined by one skilled in the art. In addition, one skilled in the art can readily design treatment/immunization schedules. For example, the non-vaccine components can be administered on days 1–14, and the vaccine antigen+adjuvant can be administered on days 7, 14, 21, and 28.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLE 1

Preparation of Plasmid Vector pCAI556 Containing the lorf2 Gene

This example illustrates the preparation of a plasmid vector pCAI556 containing the lorf2 gene.

The lorf2 gene was amplified from Chlamydia pneumoniae genomic DNA by polymerase chain reaction (PCR) using a 5' primer:

(5' ATAAGAATGCGGCCGCCACCATGTCAGGATACGCTGAACTTCC 3')

(SEQ ID NO: 3), which contains a Not I restriction site, a ribosome binding site, an initiation codon and a sequence close to the 5' end of the lorf2 coding sequence, and a 3' primer:

(5' GCGCCGGATCCCAAACGCTGAAATTATACCTA 3')

(SEQ ID NO: 4). The 3' primer includes the sequence encoding the C-terminal sequence of the lorf2 gene and a Bam HI restriction site. The stop codon was excluded and an additional nucleotide was inserted to obtain an in-frame fusion with the Histidine tag.

After amplification, the PCR fragment was purified using QIAquick™ PCR purification kit (Qiagen) and then digested with Not I and Bam HI and cloned into the pCA-Myc-His eukaryotic expression vector describe in Example 2 (FIG. 3) with transcription under control of the human CMV promoter.

EXAMPLE 2

Preparation of the Eukaryotic Expression Vector pCA/MYC-HIS

This example illustrates the preparation of the eukaryotic expression vector pCA/Myc-His.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His. The Not I/Bam HI restricted PCR fragment containing the lorf2 gene was ligated into the Not I and Bam HI restricted plasmid pCA/Myc-His to produce plasmid pCAI556 (FIG. 3).

The resulting plasmid, pCAI556, was transfered by electroporation into *E. coli* XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

EXAMPLE 3

Protection Against Intranasal *C. pneumoniae*

This example illustrates the immunization of mice to achieve protection against an intranasal challenge of *C. pneumoniae*.

It has been previously demonstrated (Yang et. al., 1993) that mice are susceptible to intranasal infection with different isolates of *C. pneumoniae*. Strain AR-39 (Grayston, 1989) was used in Balb/c mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (8 to 10 per group) were immunized intramuscularly (i.m.) plus intranasally (i.n.) with plasmid DNA containing the coding sequence of *C. pneumoniae* lorf2 gene as described in Examples 1 and 2. Saline or the plasmid vector lacking an inserted chlamydial gene was given to groups of control animals.

For i.m. immunization alternate left and right quadriceps were injected with 100 μg of DNA in 50 μl of PBS on three occasions at 0, 3 and 6 weeks. For i.n. immunization, anaesthetized mice aspirated 50 μl of PBS containing 50 μg DNA on three occasions at 0, 3 and 6 weeks. At week 8, immunized mice were inoculated i.n. with $5\times10^5$ IFU of *C. pneumoniae*, strain AR39 in 100 μl of SPG buffer to test their ability to limit the growth of a sublethal *C. pneumoniae* challenge.

Lungs were taken from mice at day 9 post-challenge and immediately homogenised in SPG buffer (7.5% sucrose, 5 mM glutamate, 12.5 mM phosphate pH 7.5). The homogenate was stored frozen at −70° C. until assay. Dilutions of the homogenate were assayed for the presence of infectious chlamydia by inoculation onto monolayers of susceptible cells. The inoculum was centriftiged onto the cells at 3000 rpm for 1 hour, then the cells were incubated for three days at 35° C. in the presence of 1 μg/ml cycloheximide. After incubation the monolayers were fixed with formalin and methanol then immunoperoxidase stained for the presence of chlamydial inclusions using convalescent sera from rabbits infected with *C. pneumoniae* and metal-enhanced DAB as a peroxidase substrate.

Figure 4:
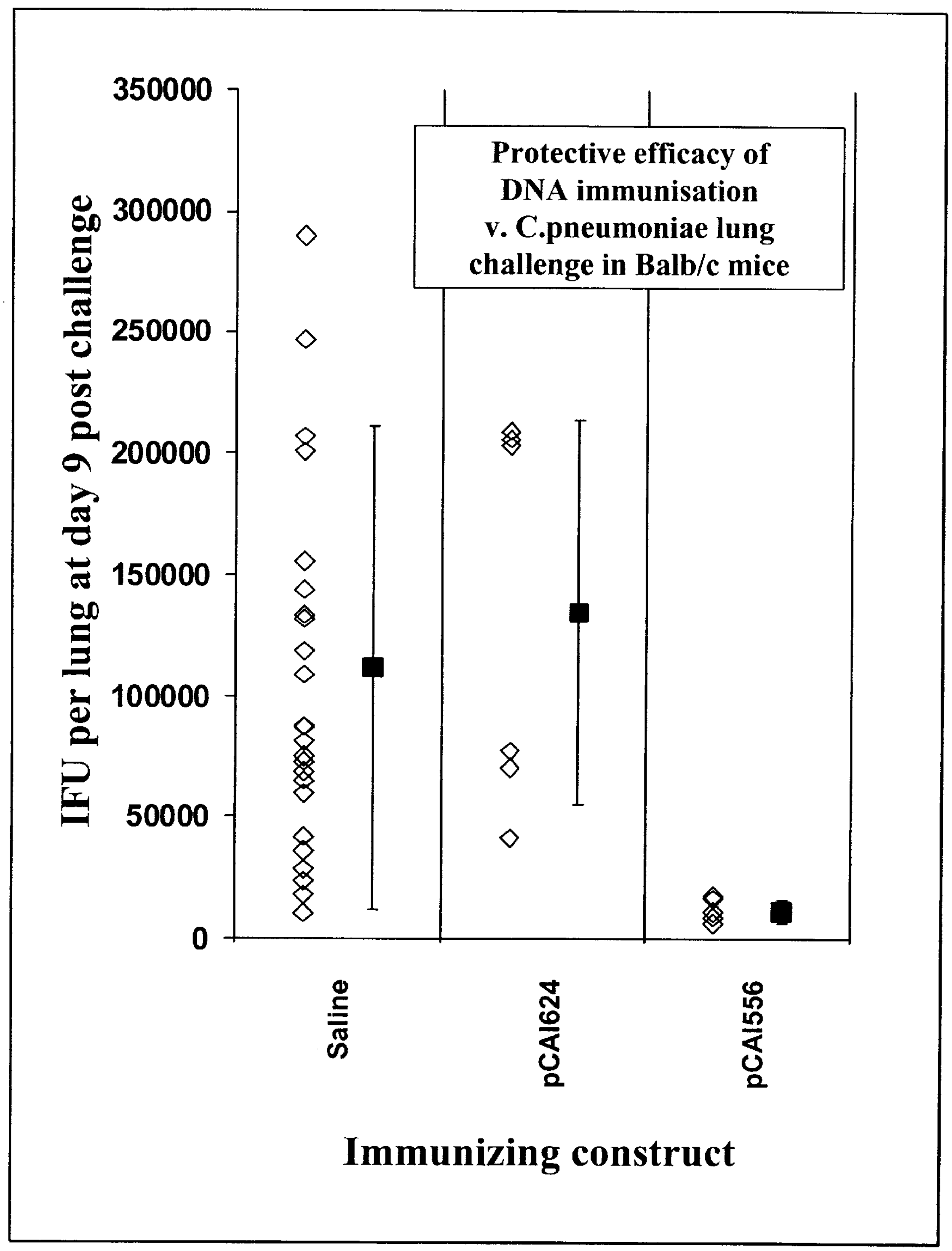
FIG. 4 illustrates protection against *C. pneumoniae* infection by pCAI556 following DNA immunization. Individual data points are shown for each animal (hollow diamonds) as well as mean and standard deviation for each group (solid squares).

FIG. 4 and Table 1 show that mice immunized i.n. and i.m. with pCAI556 had chlamydial lung titers less than 18,000 EFU/lung (mean 11,050) in 6 of 6 cases at day 9 whereas the range of values for control mice sham immunized with saline were 10,700–458,000 IFU/lung (mean 111,783) at day 9. DNA immunisation per se was not responsible for the observed protective effect since another plasmid DNA construct, pCAI624, failed to protect, with lung titers in immunized mice similar (134,600 IFU/lung) to those obtained for saline-immunized control mice. The construct pCAI624 is identical to pCAI556 except that the nucleotide sequence encoding the lorf2 gene is replaced with a *C. pneumoniae* nucleotide sequence encoding a different a 98 kDa outer membrane protein.

TABLE 1

Bacterial Load (Inclusion-Forming Units per Lung) in the Lungs of BALB/C Mice Immunized with Various DNA Immunization Constructs

| | Immunizing Construct | | |
|---|---|---|---|
| Mouse | Saline Day 9 | pCAI624 Day 9 | pCAI556 Day 9 |
| 1 | 28300 | 70200 | 11300 |
| 2 | 478800 | 206500 | 9100 |
| 3 | 201300 | 76900 | 17200 |
| 4 | 133600 | 209700 | 16200 |
| 5 | 23700 | 41200 | 6400 |
| 6 | 35900 | 203100 | 6100 |
| 7 | 108800 | | |
| 8 | 64700 | | |
| 9 | 68800 | | |
| 10 | 18200 | | |
| 11 | 59500 | | |
| 12 | 41700 | | |
| 13 | 87000 | | |
| 14 | 75000 | | |
| 15 | 118900 | | |
| 16 | 144300 | | |
| 17 | 247000 | | |
| 18 | 132000 | | |
| 19 | 207400 | | |
| 20 | 87500 | | |
| 21 | 81200 | | |
| 22 | 72800 | | |
| 23 | 10700 | | |
| 24 | 155700 | | |
| MEAN | 111783.3 | 134600 | 11050 |
| SD | 100055.3 | 79626.73 | 4781.95 |
| Wilcoxon p | | 0.3642 | 0.000383 |

Equivalents

From the foregoing detailed description of the specific embodiments of the invention, it should be apparent that a unique Chlamydia antigen has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. An isolated polynucleotide comprising a polynucleotide from a strain of Chlamydia, selected from the group consisting of:

(a) a polynucleotide comprising the nucleotide sequence of SEQ ID NO: 1; and (b) a polynucleotide which hybridizes under stringent hybridizing conditions of 6×SSC containing 50% formamide at 42° C. with a polynucleotide that has a complementary sequence to the full length of: SEQ ID NO: 1, the coding sequence of SEQ ID NO: 1, or the open reading frame(s) of SEQ ID NO: 1;

wherein said isolated polynucleotide, when administered in an immunogenically-effective amount to a mammal, induces an immune response by said mammal against Chlamydia.

2. The polynucleotide of claim 1, linked to a second nucleotide sequence encoding a fusion polypeptide.

3. The polynucleotide of claim 2 wherein the fusion polypeptide is a heterologous signal peptide.

4. The polynucleotide of claim 2 wherein the polynucleotide encodes a polypeptide comprising the amino acid sequence of the SEQ ID NO: 2.

5. An expression cassette, comprising the polynucleotide of claim 1 operably linked to a promoter.

6. An expression vector, comprising the expression cassette of claim 5.

7. A host cell, comprising the expression cassette of claim 5.

8. The host cell of claim 5, wherein said host cell is a prokaryotic cell.

9. The host cell of claim 5, wherein said host cell is a eukaryotic cell.

10. A method for producing a recombinant polypeptide comprising the amino acid sequence of having SEQ ID NO: 2, comprising:

(a) culturing a host cell of claim 7, under conditions that the allow the expression of the polypeptide; and (b) recovering the recombinant polypeptide.

* * * * *

SEQUENCE LISTING

```
<160> NUMBER OF SEQ ID NOS: 5

<210> SEQ ID NO 1
<211> LENGTH: 1550
<212> TYPE: DNA
<213> ORGANISM: Homo sapiens
<220> FEATURE:
<221> NAME/KEY: CDS
<222> LOCATION: (101)..(1366)

<400> SEQUENCE: 1

atgtttgttt cttgtagctc agtcgctttc ttttagcttt aagttttgat agcctgcttg      60

gtcttctgtt tctacactta atattgatac taaggatact atg aaa aaa cag gta       115
                                            Met Lys Lys Gln Val
                                              1               5

tat caa tgg tta gcg agt gtg gtt ctt tta gcg ctg aca att tca gga       163
Tyr Gln Trp Leu Ala Ser Val Val Leu Leu Ala Leu Thr Ile Ser Gly
                 10                  15                  20

tac gct gaa ctt cct ctc tcg gaa caa aaa gta aaa agt cac act tat       211
```

-continued

```
Tyr Ala Glu Leu Pro Leu Ser Glu Gln Lys Val Lys Ser His Thr Tyr
            25                  30                  35

aca act tta gac gaa gtc aaa gac tac tta agt aaa cgg ggt ttt gta      259
Thr Thr Leu Asp Glu Val Lys Asp Tyr Leu Ser Lys Arg Gly Phe Val
        40                  45                  50

gaa acg cga aag caa gat ggc gtt tta aga ata gca gga gat gtt aga      307
Glu Thr Arg Lys Gln Asp Gly Val Leu Arg Ile Ala Gly Asp Val Arg
    55                  60                  65

gcc cgg tgg ttg tat ttc aga gaa gat atc aaa aac ccc tca gat aaa      355
Ala Arg Trp Leu Tyr Phe Arg Glu Asp Ile Lys Asn Pro Ser Asp Lys
 70                  75                  80                  85

gat aaa tac aat ccc tta cca gta aat cgt tat cgt agt gaa ttt tat      403
Asp Lys Tyr Asn Pro Leu Pro Val Asn Arg Tyr Arg Ser Glu Phe Tyr
                90                  95                 100

ctc tat att gat tat cgc gct gag agg aac tgg ctg tct tca aag atg      451
Leu Tyr Ile Asp Tyr Arg Ala Glu Arg Asn Trp Leu Ser Ser Lys Met
            105                 110                 115

aat tgg aca gca att gca gga ggg gaa aac act gca gct ggt gtt gat      499
Asn Trp Thr Ala Ile Ala Gly Gly Glu Asn Thr Ala Ala Gly Val Asp
        120                 125                 130

atc aac aga gca ttt cta gga tat cgt ttt tat aag aat ccc gaa aca      547
Ile Asn Arg Ala Phe Leu Gly Tyr Arg Phe Tyr Lys Asn Pro Glu Thr
    135                 140                 145

cgt aca gat ttc ttt atg gaa atc gga cgt tct ggt tta gga gat ctc      595
Arg Thr Asp Phe Phe Met Glu Ile Gly Arg Ser Gly Leu Gly Asp Leu
150                 155                 160                 165

ttt gag tca gaa gtc caa ttc caa agt aat ttt gac gga cta cat ata      643
Phe Glu Ser Glu Val Gln Phe Gln Ser Asn Phe Asp Gly Leu His Ile
                170                 175                 180

tat tgg act cga gaa ctt tct aag gac tat cct tat caa gtg att gtt      691
Tyr Trp Thr Arg Glu Leu Ser Lys Asp Tyr Pro Tyr Gln Val Ile Val
            185                 190                 195

cat gga ggt cct ttc gtc gtg aac atg aca aaa aaa cat tat gct tgg      739
His Gly Gly Pro Phe Val Val Asn Met Thr Lys Lys His Tyr Ala Trp
        200                 205                 210

gtt gta gaa ggg att ctc aat cgt ttg cct aaa cag ttt ttt gtg aaa      787
Val Val Glu Gly Ile Leu Asn Arg Leu Pro Lys Gln Phe Phe Val Lys
    215                 220                 225

tgt agt gtt gtc gac tgg aac aca ttc gtt cct tca gaa acc tcc act      835
Cys Ser Val Val Asp Trp Asn Thr Phe Val Pro Ser Glu Thr Ser Thr
230                 235                 240                 245

aca gaa aaa gct gct aca aac gct atg aaa tac aaa tac tgt gtt tgg      883
Thr Glu Lys Ala Ala Thr Asn Ala Met Lys Tyr Lys Tyr Cys Val Trp
                250                 255                 260

cag tgg ctc gtc gga aag cat agt cag gtt cct tgg atc aat gga cag      931
Gln Trp Leu Val Gly Lys His Ser Gln Val Pro Trp Ile Asn Gly Gln
            265                 270                 275

aaa aag cct cta tat ctt tat gga gct ttc tta atg aac cct tta gca      979
Lys Lys Pro Leu Tyr Leu Tyr Gly Ala Phe Leu Met Asn Pro Leu Ala
        280                 285                 290

aag gct acg aag act acg tta aat gga aaa gaa aac cta gct tgg ttt     1027
Lys Ala Thr Lys Thr Thr Leu Asn Gly Lys Glu Asn Leu Ala Trp Phe
    295                 300                 305

att gga gga act tta ggg gga ctc aga aaa gct gga gac tgg tct gcc     1075
Ile Gly Gly Thr Leu Gly Gly Leu Arg Lys Ala Gly Asp Trp Ser Ala
310                 315                 320                 325

aca gta cgt tat gag tat gtc gaa gcc ttg tcg gtt cca gaa ata gat     1123
Thr Val Arg Tyr Glu Tyr Val Glu Ala Leu Ser Val Pro Glu Ile Asp
                330                 335                 340
```

-continued

```
gtt tca ggg att ggc cgt ggt aat tta tta aag ttt tgg ttc gcc caa      1171
Val Ser Gly Ile Gly Arg Gly Asn Leu Leu Lys Phe Trp Phe Ala Gln
            345                 350                 355

gca att gct gct aac tat gat cct aaa gag gct aat ggt ttt aca aat      1219
Ala Ile Ala Ala Asn Tyr Asp Pro Lys Glu Ala Asn Gly Phe Thr Asn
        360                 365                 370

tat aaa gga ttt tcc gct cta tat atg tat ggc atc aca gat tct cta      1267
Tyr Lys Gly Phe Ser Ala Leu Tyr Met Tyr Gly Ile Thr Asp Ser Leu
    375                 380                 385

tca ttc aga gct tat ggg gct tac tcc aaa cca gca aac gat aaa ctc      1315
Ser Phe Arg Ala Tyr Gly Ala Tyr Ser Lys Pro Ala Asn Asp Lys Leu
390                 395                 400                 405

ggc agt gat ttt act ttc cga aag ttt gat cta ggt ata att tca gcg      1363
Gly Ser Asp Phe Thr Phe Arg Lys Phe Asp Leu Gly Ile Ile Ser Ala
                410                 415                 420

ttt taagtcaaat tttaataaaa tctttaaaaa caggctcgca ttaattatta           1416
Phe

gtgagagctt ttttttattt ttttataata aaactaaaag atttttatta ttttttgagt    1476

ttttatggtt aatcctattg gtccaggtcc tatagacgaa acagaacgca cacctcccgc    1536

agatctttct gctc                                                      1550


<210> SEQ ID NO 2
<211> LENGTH: 422
<212> TYPE: PRT
<213> ORGANISM: Homo sapiens

<400> SEQUENCE: 2

Met Lys Lys Gln Val Tyr Gln Trp Leu Ala Ser Val Val Leu Leu Ala
  1               5                  10                  15

Leu Thr Ile Ser Gly Tyr Ala Glu Leu Pro Leu Ser Glu Gln Lys Val
            20                  25                  30

Lys Ser His Thr Tyr Thr Thr Leu Asp Glu Val Lys Asp Tyr Leu Ser
        35                  40                  45

Lys Arg Gly Phe Val Glu Thr Arg Lys Gln Asp Gly Val Leu Arg Ile
    50                  55                  60

Ala Gly Asp Val Arg Ala Arg Trp Leu Tyr Phe Arg Glu Asp Ile Lys
 65                  70                  75                  80

Asn Pro Ser Asp Lys Asp Lys Tyr Asn Pro Leu Pro Val Asn Arg Tyr
                85                  90                  95

Arg Ser Glu Phe Tyr Leu Tyr Ile Asp Tyr Arg Ala Glu Arg Asn Trp
            100                 105                 110

Leu Ser Ser Lys Met Asn Trp Thr Ala Ile Ala Gly Gly Glu Asn Thr
        115                 120                 125

Ala Ala Gly Val Asp Ile Asn Arg Ala Phe Leu Gly Tyr Arg Phe Tyr
    130                 135                 140

Lys Asn Pro Glu Thr Arg Thr Asp Phe Phe Met Glu Ile Gly Arg Ser
145                 150                 155                 160

Gly Leu Gly Asp Leu Phe Glu Ser Glu Val Gln Phe Gln Ser Asn Phe
                165                 170                 175

Asp Gly Leu His Ile Tyr Trp Thr Arg Glu Leu Ser Lys Asp Tyr Pro
            180                 185                 190

Tyr Gln Val Ile Val His Gly Gly Pro Phe Val Val Asn Met Thr Lys
        195                 200                 205

Lys His Tyr Ala Trp Val Val Glu Gly Ile Leu Asn Arg Leu Pro Lys
    210                 215                 220
```

-continued

```
Gln Phe Phe Val Lys Cys Ser Val Val Asp Trp Asn Thr Phe Val Pro
225                 230                 235                 240

Ser Glu Thr Ser Thr Thr Glu Lys Ala Ala Thr Asn Ala Met Lys Tyr
                245                 250                 255

Lys Tyr Cys Val Trp Gln Trp Leu Val Gly Lys His Ser Gln Val Pro
            260                 265                 270

Trp Ile Asn Gly Gln Lys Lys Pro Leu Tyr Leu Tyr Gly Ala Phe Leu
        275                 280                 285

Met Asn Pro Leu Ala Lys Ala Thr Lys Thr Thr Leu Asn Gly Lys Glu
    290                 295                 300

Asn Leu Ala Trp Phe Ile Gly Gly Thr Leu Gly Gly Leu Arg Lys Ala
305                 310                 315                 320

Gly Asp Trp Ser Ala Thr Val Arg Tyr Glu Tyr Val Glu Ala Leu Ser
                325                 330                 335

Val Pro Glu Ile Asp Val Ser Gly Ile Gly Arg Gly Asn Leu Leu Lys
            340                 345                 350

Phe Trp Phe Ala Gln Ala Ile Ala Ala Asn Tyr Asp Pro Lys Glu Ala
        355                 360                 365

Asn Gly Phe Thr Asn Tyr Lys Gly Phe Ser Ala Leu Tyr Met Tyr Gly
    370                 375                 380

Ile Thr Asp Ser Leu Ser Phe Arg Ala Tyr Gly Ala Tyr Ser Lys Pro
385                 390                 395                 400

Ala Asn Asp Lys Leu Gly Ser Asp Phe Thr Phe Arg Lys Phe Asp Leu
                405                 410                 415

Gly Ile Ile Ser Ala Phe
            420


<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: PCR Primer
      Sequence

<400> SEQUENCE: 3

ataagaatgc ggccgccacc atgtcaggat acgctgaact tcc                    43


<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: PCR Primer
      Sequence

<400> SEQUENCE: 4

gcgccggatc ccaaacgctg aaattatacc ta                                32


<210> SEQ ID NO 5
<211> LENGTH: 1550
<212> TYPE: DNA
<213> ORGANISM: Homo sapiens

<400> SEQUENCE: 5

tacaaacaaa gaacatcgag tcagcgaaag aaaatcgaaa ttcaaaacta tcggacgaac     60

cagaagacaa agatgtgaat tataactatg attcctatga tactttttttg tccatatagt   120

taccaatcgc tcacaccaag aaaatcgcga ctgttaaagt cctatgcgac ttgaaggaga    180
```

-continued

```
gagccttgtt tttcattttt cagtgtgaat atgttgaaat ctgcttcagt ttctgatgaa    240

ttcatttgcc ccaaaacatc tttgcgcttt cgttctaccg caaaattctt atcgtcctct    300

acaatctcgg gccaccaaca taaagtctct tctatagttt ttggggagtc tatttctatt    360

tatgttaggg aatggtcatt tagcaatagc atcacttaaa atagagatat aactaatagc    420

gcgactctcc ttgaccgaca gaagtttcta cttaacctgt cgttaacgtc ctcccctttt    480

gtgacgtcga ccacaactat agttgtctcg taaagatcct atagcaaaaa tattcttagg    540

gctttgtgca tgtctaaaga aatacctta gcctgcaaga ccaaatcctc tagagaaact     600

cagtcttcag gttaaggttt cattaaaact gcctgatgta tatataacct gagctcttga    660

aagattcctg ataggaatag ttcactaaca agtacctcca ggaaagcagc acttgtactg    720

tttttttgta atacgaaccc aacatcttcc ctaagagtta gcaaacggat ttgtcaaaaa    780

acactttaca tcacaacagc tgaccttgtg taagcaagga agtctttgga ggtgatgtct    840

ttttcgacga tgtttgcgat actttatgtt tatgacacaa accgtcaccg agcagccttt    900

cgtatcagtc caaggaacct agttacctgt ctttttcgga gatatagaaa tacctcgaaa    960

gaattacttg ggaaatcgtt tccgatgctt ctgatgcaat ttaccttttc ttttggatcg   1020

aaccaaataa cctccttgaa atccccctga gtcttttcga cctctgacca gacggtgtca   1080

tgcaatactc atacagcttc ggaacagcca aggtctttat ctacaaagtc cctaaccggc   1140

accattaaat aatttcaaaa ccaagcgggt tcgttaacga cgattgatac taggatttct   1200

ccgattacca aaatgtttaa tatttcctaa aaggcgagat atatacatac cgtagtgtct   1260

aagagatagt aagtctcgaa taccccgaat gaggtttggt cgtttgctat ttgagccgtc   1320

actaaaatga aaggctttca aactagatcc atattaaagt cgcaaaattc agtttaaaat   1380

tattttagaa atttttgtcc gagcgtaatt aataatcact ctcgaaaaaa aaataaaaaa   1440

tattattttg attttctaaa aataataaaa aactcaaaaa taccaattag gataaccagg   1500

tccaggatat ctgctttgtc ttgcgtgtgg agggcgtcta gaaagacgag               1550
```